United States Patent [19]
Karpf et al.

[11] Patent Number: 5,892,040
[45] Date of Patent: Apr. 6, 1999

[54] PROCESS FOR THE MANUFACTURE OF A TRICYCLIC COMPOUND

[75] Inventors: Martin Karpf; Rene Trussardi, both of Basel, Switzerland

[73] Assignee: Pfizer. Inc, New York, N.Y.

[21] Appl. No.: 492,039

[22] PCT Filed: Jan. 19, 1994

[86] PCT No.: PCT/EP94/00147

§ 371 Date: Jan. 4, 1996

§ 102(e) Date: Jan. 4, 1996

[87] PCT Pub. No.: WO94/17074

PCT Pub. Date: Aug. 4, 1994

[30] Foreign Application Priority Data

Jan. 23, 1993 [EP] European Pat. Off. .............. 93101031

[51] Int. Cl.$^6$ ...................... C07D 498/06; C07D 215/58; A61K 31/535; C07C 243/28
[52] U.S. Cl. .......................... 544/363; 544/66; 544/344; 544/234; 546/156
[58] Field of Search ............................ 544/363, 66, 344; 546/156

[56] References Cited

U.S. PATENT DOCUMENTS

| | | | |
|---|---|---|---|
| 4,666,920 | 5/1987 | Grohe et al. | 514/312 |
| 4,689,423 | 8/1987 | Beylin et al. | 560/51 |
| 4,753,925 | 6/1988 | Grohe et al. | 514/254 |
| 4,769,492 | 9/1988 | Kaieda et al. | 562/479 |
| 4,769,493 | 9/1988 | Ito et al. | 562/480 |
| 4,782,180 | 11/1988 | Wemple et al. | 562/479 |
| 4,801,584 | 1/1989 | Yokose et al. | 514/183 |
| 4,831,190 | 5/1989 | Ataka et al. | 362/474 |
| 4,864,023 | 9/1989 | Yokose et al. | 544/66 |

FOREIGN PATENT DOCUMENTS 0259804  3/1988  European Pat. Off. .

OTHER PUBLICATIONS

Research Disclosure, 'Process for the manufacture . . . ' No. 291, 1988, New York USA, pp. 548–551.
Grohe, K., et al. 'Synthese von . . . ' Liebigs Annalen der Chemie., No. 10, 1987, Weinheim DE, pp. 871–879.
Derwent Abstract 94–062042/08, Katayama Seiyakusho KK (94.01.25).

Primary Examiner—Mukund J. Shah
Assistant Examiner—Sabiha Qazi
Attorney, Agent, or Firm—Peter C. Richardson; Paul H. Ginsburg; Raymond M. Speer

[57] ABSTRACT

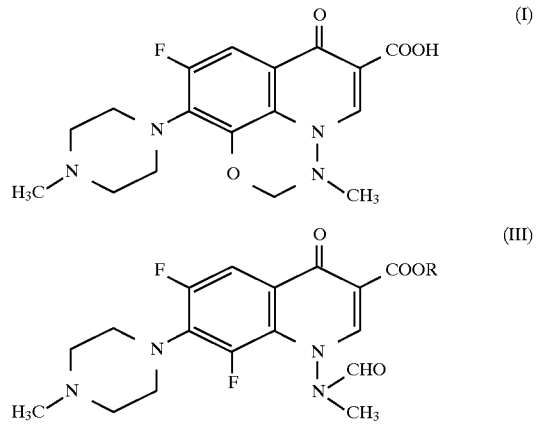

A process for preparing a compound of formula (I) or a phamaceutically-acceptable salt thereof, comprising: 1) reacting a compound. of formula (III), in which R is a straight or branched chain alkyl having from one to four carbon atoms, with an alkali metal hydroxide in an aqueous medium at a temperature of about 80° to 120° C. and time of about 20 to 100 hours to form a reaction product; 2) cyclizing the reaction product of step 1) with formic acid and formaldehyde to form a formiate compound; and 3) neutralizing the formiate compound of step 2) with an aqueous base.

27 Claims, No Drawings

PROCESS FOR THE MANUFACTURE OF A TRICYCLIC COMPOUND

This application is a 371 of PCT/EP94/00147, filed Jan. 19, 1994.

The present invention relates to a new process for the manufacture of a tricyclic compound, i.e. a pyrido[3,2,1-ij]-1,3,4-benzoxadiazine derivative of the formula

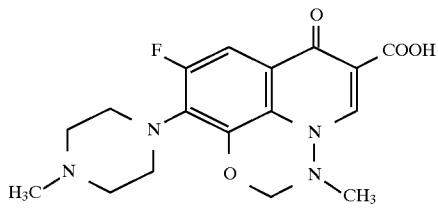

and its pharmaceutically acceptable salts. Also included in the present invention are novel intermediates useful in this process.

The compound of formula I, 9-fluoro-2,3-dihydro-3-methyl-10-(4-methyl-1-piperazinyl)-7-oxo-7H-pyrido[3,2,1-ij]-1,3,4-benzoxadiazine-6-carboxylic acid and its pharmaceutically acceptable salts are antibacterially active and useful as effective ingredients in antibacterial agents. They are described in European Patent Specification No. 259 804 together with a process for their manufacture. The process described therein is unpracticable for large scale manufacture, however, in that a multistep process is used which requires high temperatures and untechnical reagents (e.g. 0-(2,4-dinitrophenyl)-hydroxylamine for amination involves danger of explosion) resulting in low over-all yields.

The present invention provides a practical process for manufacturing the compound of formula I in superior yields. Starting from the acid chloride of 2, 3, 4, 5-tetrafluorobenzoic acid, the process can be depicted by the following flow sheet (Scheme I).

Note that Research Disclosure No. 291, 1988, pages 548–551 discloses an alternative route also starting from 2, 3, 4, 5-tetrafluorobenzoic acid. Also that Liebigs Annalen Der Chemie, No. 10, 1987, page 875 discloses the compound 2-(2, 3, 4, 5-tetrafluorobenzoyl)-3-(2-formyl-2-methylhydrazino) acrylic acid-ethyl ester.

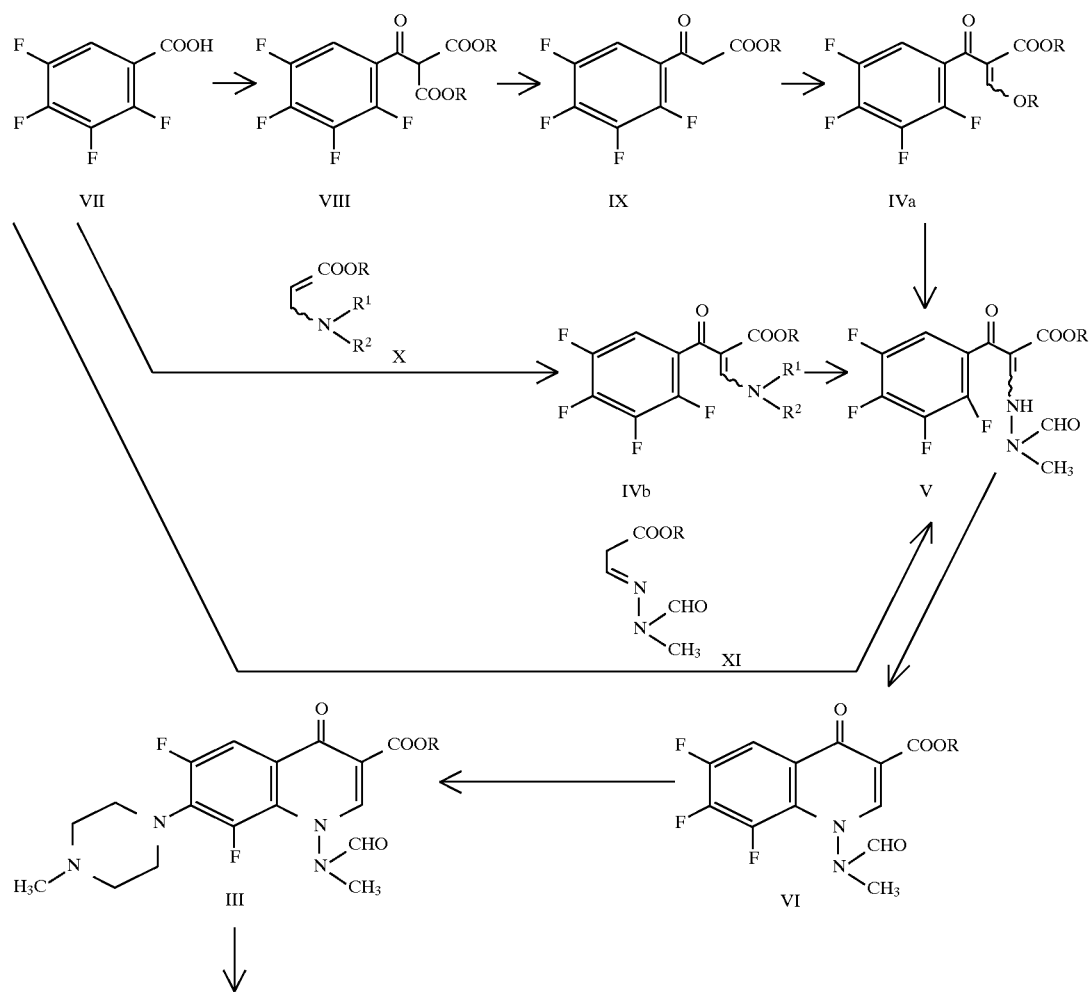

Scheme I

-continued
Scheme I

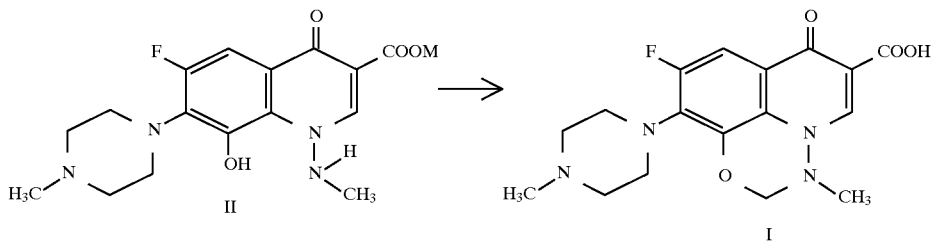

In Scheme I R represents alkyl of from one to four carbon atoms, preferably methyl or ethyl, $NR^1R^2$ is N,N'-(dicyclohexyl)amino, N-methyl-N'-benzyl-amino or 4-methyl-piperazinyl, M is the cation of an alkali metal hydroxide, and the wavy line (∼) indicates two stereospecific possibilities.

As is seen from the above Reaction Scheme I the manufacture of compound I proceeds over a key intermediate of formula V which is obtained through 3 alternative pathways, the preferable pathways, due to their superior yields, being pathways VII→IVb→V and VII-XI→V.

The various process steps will be discussed in detail hereinbelow.

VII→VIII 2,3,4,5-Tetrafluorobenzoic acid chloride VII is converted to the acylated malonic ester VIII via a metal salt of a malonic acid ester, preferably via the magnesium salt of diethyl malonate.

The so-obtained acylated malonic acid ester VIII is subjected to acidic hydrolysis, preferably by refluxing with a sulfonic acid, such as p-toluene sulfonic acid in aqueous medium, to yield the monoester IX.

IX→IVa

Said monoester IX is converted to the alkoxyacrylic acid ester IVa by refluxing with a trialkyl orthoformate (preferably triethyl orthoformate) in an organic solvent, which is preferably acetic acid anhydride.

IVA→V

The alkoxyacrylic acid IVa is reacted with N-amino-N-methyl-formamide in an inert organic solvent, preferably toluene at about room temperature to yield product V.

V→VI

Compound V is cyclized to the 1-(N-methylformamido)-quinoline derivative VI by heating the reaction solution, preferably up to reflux temperature, preferably in the presence of a base, such as a lower trialkyl-amine, e.g. triethylamine, or an alkali metal carbonate, e.g. sodium carbonate.

VI→III

The compound VI is reacted with N-methylpiperazine to yield the substitution product III, preferably at reflux temperature in the same solvent as the previous reaction and under the same basic conditions.

III→II

Compound III is reacted with an alkali metal hydroxide, preferably potassium hydroxide, in an aqueous medium at about 80° C. to 120° C., preferably reflux, for about 20 to 100 hours. In this reaction surprisingly a fluorine/hydroxy exchange is effected in position 8, which goes to practical completion by utilizing at least about 10 mol equivalents of alkali metal hydroxide and increasing the reaction time to about 70 to 100 hours. The alkali metal hydroxide is preferably present in a concentration of about 10 to 20% by weight of the aqueous solution.

II→I

The 1-(N-methylamino)-quinoline derivative II obtained in this manner is cyclized to the desired end product I, viz. 9-fluoro-2,3-dihydro-3-methyl-10-(4-methyl-1-piperazinyl)-7-oxo-7H-pyrido[3,2,1-ij]-1,3,4-benzoxadiazine-6-carboxylic acid, by treatment with formic acid and formaldehyde, preferably with an excess of both of 85% aqueous formic acid and 25–50% aqueous formaldehyde.

The end product is obtained as formiate salt, which is neutralized to the corresponding carboxylic acid form by means of an aqueous base, such as aqueous sodium hydroxide or aqueous ammonia.

Alternative pathways to arrive at the intermediate V:

VII→IVb→V 2,3,4,5-Tetrafluorobenzoic acid VII is acylated (via its acid chloride) with the aminoacrylic ester X in the presence of a base, preferably a tertiary amine, e.g. triethylamine, in an inert organic solvent, preferably toluene at elevated temperature, preferably reflux. The so obtained intermediate IVb is reacted with N-amino-N-methylformamide in an inert organic solvent, preferably toluene at about room temperature to yield the condensation product V.

VII→V 2,3,4,5-Tetrafluorobenzoic acid VII is reacted (via its acid chloride) with the 3-(formylmethylhydrazono)-propionic ester XI and a magnesium lower alkanolate, e.g. magnesium ethylate, in an inert organic solvent, such as ethyl acetate, at low temperature, preferably in the range of 0°–10° C., followed by acidification, e.g. with formic acid, to yield compound V.

The above reactions in Scheme I are preferably effected in a "direct procedure", i.e. without isolation and purification of any of the intermediates obtained.

EXAMPLE 1

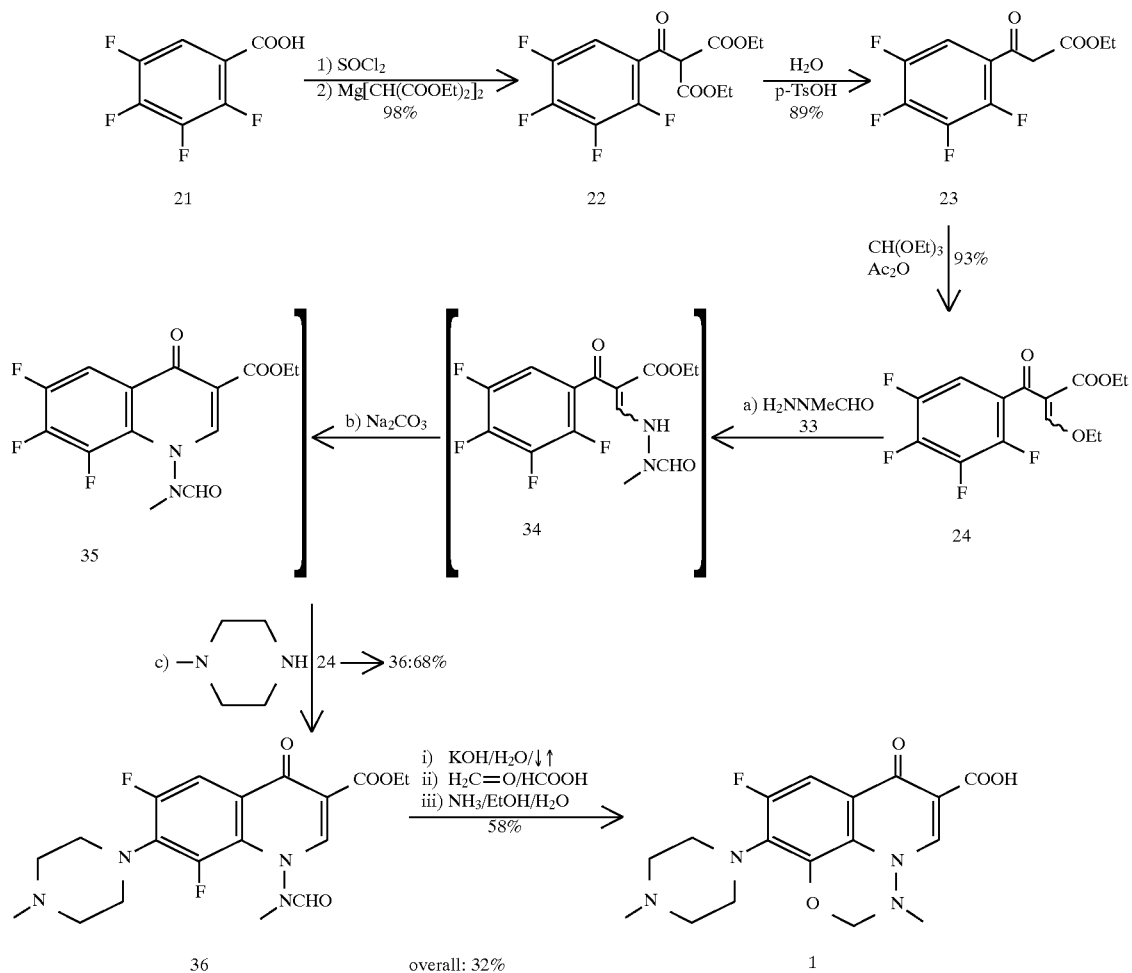

Synthesis of diethyl (2,3,4,5)-tetrafluorobenzoyl)malonate (22)

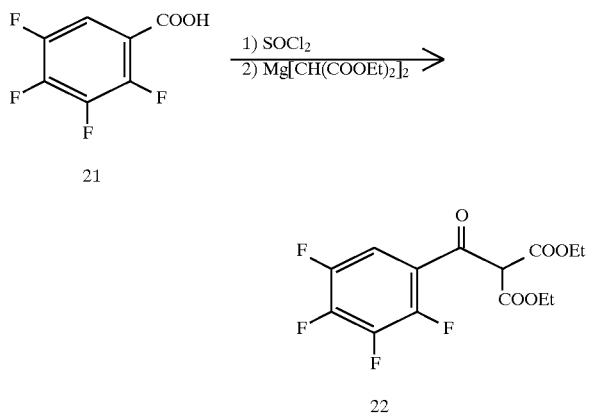

a) Acid Chloride Formation

In a 18 liter glass reactor equipped with a mechanical stirrer, a thermometer, an inert gas supply and a reflux condenser connected to a gas absorption unit for HCl and SO₂ 1553 g of 2,3,4,5-tetrafluorobenzoic acid (21, 8.00 mol) were suspended at room temperature under argon with stirring in 4000 ml of toluene. After addition of 1142 g of thionyl chloride (9.6 mol) and 11 ml of dimethyl formamide the reaction mixture was heated to reflux for 2.5 hrs at 93°–95° C. At reduced pressure about 1000 ml of a thionyl chloride/toluene mixture was distilled within 60 min from the reaction vessel through a descending Liebig condenser. The remaining yellow solution containing the acid chloride of 21 was kept under argon at 4° C.

b) Acylation of Diethyl Malonate

In an 18 liter glass reactor equipped with a mechanical stirrer, a thermometer, a reflux condenser, an inert gas supply and a metering pump 195 g of magnesium turnings (8.00 mol) were covered under argon and with stirring with 400 ml of ethanol. After addition of 7 ml of carbon tetrachloride the evolution of gas started and the temperature rose to 50° C. In the temperature range of 50°–70° C. a solution of 1282 g of diethyl malonate (8.00 mol) dissolved in a mixture of 3200 ml of toluene and 1600 ml of ethanol was continuously added over a period of 2 hours. The reaction mixture was stirred for 3 hours at 70° C. and cooled to −5° C. To this mixture 5000 ml of the 2,3,4,5-tetrafluorobenzoic acid chloride solution in toluene (ca. 8.00 mol, prepared as described under a), was added dropwise over a period of 2 hours keeping the temperature in the range of 0°–5° C. The resulting green viscous solution was stirred for 30 min at 0° C. and then treated in the course of 1 hour with a solution of 200 ml of concentrated sulfuric acid (3.7 mol) mixed with 3200 ml of ice water (deionized), keeping the temperature at 0° C. The two-phase mixture was transferred to an extraction vessel, mixed with 5000 ml of water (deionized) and extracted. The aqueous phase was transferred for extraction to a second, then to a third extraction vessel, each containing 4000 ml, in total 8000 ml, of toluene. The aqueous phase was discarded and the 3 organic layers were consecutively washed with 2 portions of 3000 ml, in total 6000 ml, of water (deionized). The aqueous layers were discarded, the organic layers combined and evaporated in a rotary evaporator first at 50°/16 torr, then dried at 50°/2 torr to give as a crude product 2648 g (98%) of 22 as a yellowish liquid. This material was used in the next step without further purification.

Synthesis of ethyl (2,3,4,5-tetrafluorobenzoyl)acetate (23)

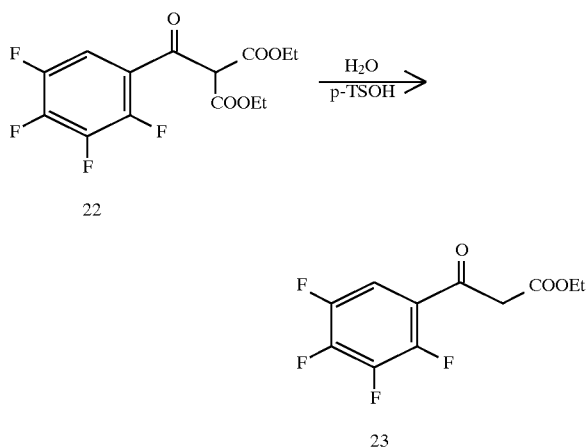

In an 18 liter glass reactor equipped with a mechanical stirrer, a thermometer, a reflux condenser and an inert gas supply a mixture of 2648 g of diethyl (2,3,4,5-tetrafluorobenzoyl)malonate (22, 7.88 mol, crude product from the previous step) and 3000 ml of water (deionized) was stirred at room temperature under argon. After the addition of 5 g of p-toluene sulfonic acid monohydrate the orange emulsion was heated to reflux for 11 hours. The reaction mixture was cooled to room temperature, extracted with 3 portions of 4000 ml, in total 12000 ml, of methylene chloride and the aqueous phase was discarded. The three organic layers were consecutively extracted, first with 3000 ml of 3% aqueous sodium bicarbonate, then with 2 portions of 3000 ml, in total 6000 ml, of water (deionized). The aqueous phases were discarded and the 3 organic phases combined, evaporated to a volume of ca. 4000–5000 ml at 50°/200 torr, dried over 400 g of magnesium sulfate and filtered. The filter cake was washed with 2 portions of ca. 300 ml, in total ca. 600 ml, of methylene chloride and the combined filtrates evaporated in a rotary evaporator at 50°/110 torr, then dried during 2 hrs at 50°/0.5 torr to give as a crude product 1856 g (89%) of 23 as an orange oil containing crystals (from 100 g of this crude product 63 g of analytically pure 23 were obtained as white crystals, m.p. 43°–46° C. by crystallization from 100 ml of ethanol at 20° C.). The crude product was used in the next step without further purification.

Sythesis of ethyl 3-ethoxy-2-(2,3,4,5-tetrafluorobenzoyl)acrylate (24)

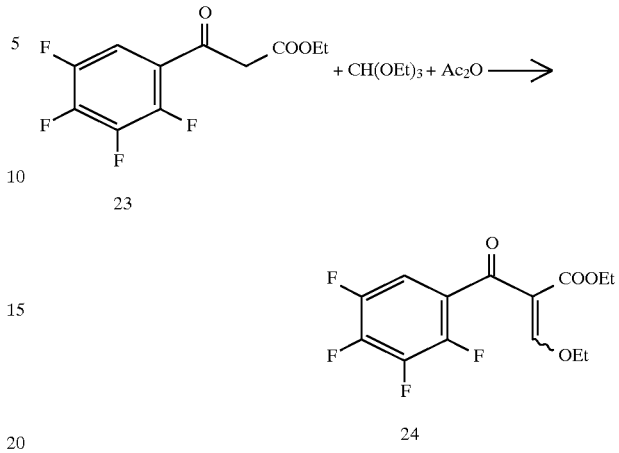

In an 18 liter glass reactor equipped with a mechanical stirrer, a thermometer, a reflux condenser and an inert gas supply 3030 g of ethyl (2,3,4,5-tetrafluorobenzoyl)acetate (23, 11.47 mol, crude product from the previous step) were dissolved in a mixture of 2638 g of triethyl orthoformate (17.8 mol) and 3056 g of acetic anhydride (29.9 mol) and heated to reflux for 3 hours. From the reaction mixture 3000 ml of liquid were distilled over about 1 hour using a descending Liebig condenser at reduced pressure. The brown residue was evaporated in a rotary evaporator first at 70° C./10 torr, then at 70° C./0.1 torr to yield a crude product 3426 g (93%) of 24 as a brown liquid. The crude product was used in the next step without further purification.

Synthesis of N-amino-N-methylformamide (33)

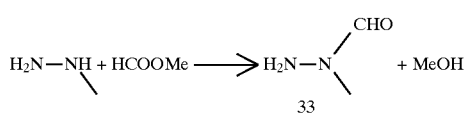

In an 18 liter glass reactor equipped with a mechanical stirrer, a 2 liter dropping fennel, a thermometer and an inert gas supply 1382 g of methyl-hydrazine (30 mol) were treated under argon with stirring and intensive cooling with 1982 g of methyl formate (33 mol) over 75 min keeping the temperature in the range of 16°–20° C. The dear, colourless reaction mixture was stirred for 30 min and evaporated in a rotary evaporator at 40° C./16 torr. The remaining colourless liquid (2270 g) was distilled through a 40 cm distillation column at 0.25–0.30 torr. After a first fraction (b.p. 37°–68° C., 21 g) which was discarded, the main fraction boiling at 54–64° C. yielded as the product 2103 g (95%) of 33 as a colourless liquid, b.p. 54°–64° C./0.25–0.30 torr.

Synthesis of ethyl 6,8-difluoro-1,4-dihydro-1-(N-methylformamido)-7-(4-methyl-1-piperazinyl)-4-oxo-3-quinolinecarboxylate (36)

step a)

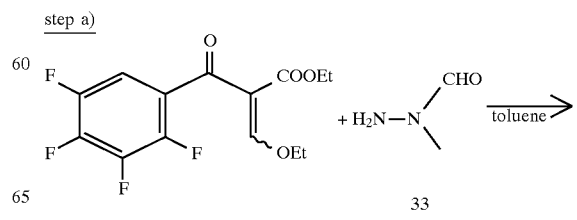

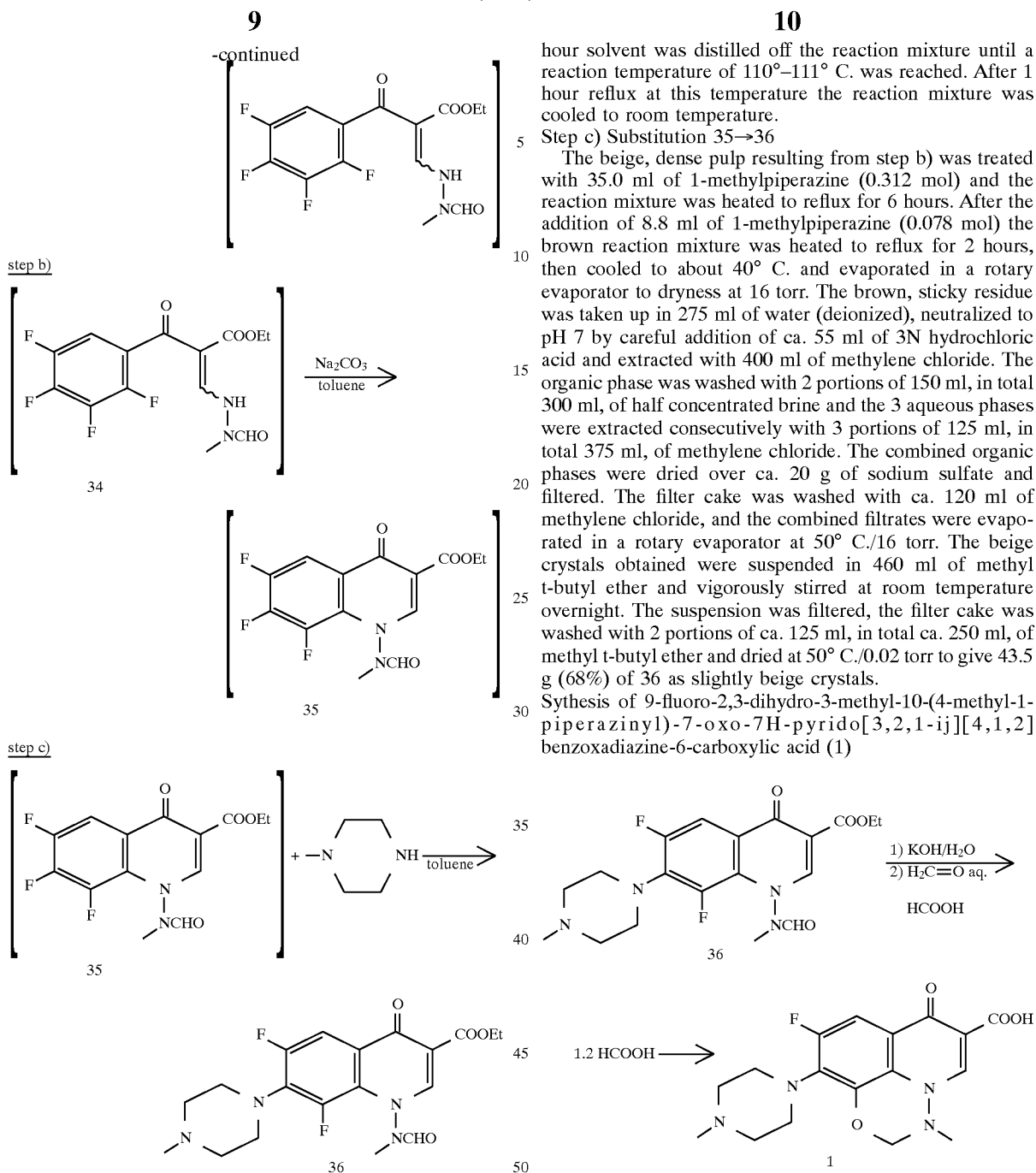

hour solvent was distilled off the reaction mixture until a reaction temperature of 110°–111° C. was reached. After 1 hour reflux at this temperature the reaction mixture was cooled to room temperature.

Step c) Substitution 35→36

The beige, dense pulp resulting from step b) was treated with 35.0 ml of 1-methylpiperazine (0.312 mol) and the reaction mixture was heated to reflux for 6 hours. After the addition of 8.8 ml of 1-methylpiperazine (0.078 mol) the brown reaction mixture was heated to reflux for 2 hours, then cooled to about 40° C. and evaporated in a rotary evaporator to dryness at 16 torr. The brown, sticky residue was taken up in 275 ml of water (deionized), neutralized to pH 7 by careful addition of ca. 55 ml of 3N hydrochloric acid and extracted with 400 ml of methylene chloride. The organic phase was washed with 2 portions of 150 ml, in total 300 ml, of half concentrated brine and the 3 aqueous phases were extracted consecutively with 3 portions of 125 ml, in total 375 ml, of methylene chloride. The combined organic phases were dried over ca. 20 g of sodium sulfate and filtered. The filter cake was washed with ca. 120 ml of methylene chloride, and the combined filtrates were evaporated in a rotary evaporator at 50° C./16 torr. The beige crystals obtained were suspended in 460 ml of methyl t-butyl ether and vigorously stirred at room temperature overnight. The suspension was filtered, the filter cake was washed with 2 portions of ca. 125 ml, in total ca. 250 ml, of methyl t-butyl ether and dried at 50° C./0.02 torr to give 43.5 g (68%) of 36 as slightly beige crystals.

Sythesis of 9-fluoro-2,3-dihydro-3-methyl-10-(4-methyl-1-piperazinyl)-7-oxo-7H-pyrido[3,2,1-ij][4,1,2]benzoxadiazine-6-carboxylic acid (1)

Step a) Substitution 24→34

In a 500 ml 4-necked round bottom flask equipped with a mechanical stirrer, a reflux condenser, a thermometer and an inert gas supply 50.0 g of ethyl 3-ethoxy-2-(2,3,4,5-tetrafluorobenzoyl)acrylate (24, 0.156 mol, crude product from previous step) were dissolved under nitrogen and with stirring in 150 ml of toluene. To this solution were added 11.71 g of N-amino-N-methylformamide (33, 0.158 mol) whereby the temperature rose to 37° C. The temperature was adjusted to room temperature in an ice bath and the pale yellow solution was stirred for 17 hours.

Step b) Cyclization 34→35

To the above solution 18.23 g of sodium carbonate (0.172 mol) were added and the beige suspension was heated to reflux. After the boiling point was reached at about 80° C., 100 ml of toluene were added, and over a period of ca. 1

In a 2 liter steel reactor equipped with a mechanical stirrer, a thermo-meter, a descending Liebig condenser and an inert gas supply 99.0 g of potassium hydroxide (ca. 1.5 mol) were dissolved under argon and with stirring in 1000 ml of water (deionized). After addition of 204.2 g of ethyl 6,8-difluoro-1,4-dihydro-1-(N-methylformamido)-7-(4-methyl-1-piperazinyl)-4-oxo-3-quinolinecarboxylate (36, 0.5 mol) the suspension was heated in an oil bath until dissolution was complete. From this solution an ethanol/water mixture was distilled until the b.p. remained constant for 15 min. After replacing the descending Liebig condenser by a reflux condenser a solution of 231.0 g of potassium hydroxide (ca. 3.5 mol) in 260 ml of water (deionized) was added at 90°–95° C. over a period of 10 min, and the reaction mixture was heated in an oil bath of 135° C. during 72 hrs to reflux (reaction temperature 104° C.). The dark brown solution was cooled to 40° C., diluted with 250 ml of water (deionized) and treated over a period of ca. 30 min with 340 ml of 85% formic acid (ca. 7.5 mol) without exceeding a temperature of 50° C. In the temperature range of 40°–45° C. 75,0 ml of aqueous 36.5% formaldehyde (ca. 1.0 mol) were added over 10 min. The pink suspension was heated to 70° C. and stirred at this temperature for 30 min. After cooling to 0°–5° C. and stirring at this temperature for 30 min the suspension was filtered with vigorous so suction, the filter cake was washed with 100 ml of water (deionized, precooled to ca. 5° C.) and vigorously sucked.

Work-up with Ammonia:

The wet, grey and crude dihydroformate of 1 (ca. 260 g) was suspended with stirring in a mixture of 750 ml of ethanol and 265 ml of water (deionized) and dissolved by addition of 90 ml of 25% aqueous ammonia (ca. 2.16 mol) over a period of 30 min. The dark, slightly turbid solution was filtered through a glass fiber filter. From the clear, black filtrate a total of 600 ml of a solvent mixture was distilled through a descending condenser over a period of ca. 1.5 hours whereby the boiling point rose from 78° to 81° C. and the solid product 1 started to precipitate after distillation of about 250 ml. The grey-yellowish suspension was cooled to 0°–5° C., stirred at this temperature for 30 min and filtered through a glass filter funnel. The yellowish filter cake was washed with 3 portions of 150 ml, in total 450 ml, of ethanol, intensely sucked and dried at 50° C./30 torr for 18 hours to give as the product 104.3 g (58%) of 1 as a yellow powder, m.p. 268°–271° C. (dec.), MS m/z 362 (M+).

Work-up with Sodium Hydroxide:

735 g of dried dihydroformate of 1 (obtained after washing with dioxan and drying at 50° C./16 torr for 15 hours) were suspended in 41.2 g of potassium dihydrogen phosphate in 3000 ml of deionized water; to this suspension 1500 ml of ethanol and 4500 ml of methylene chloride were added. To the so-formed fine suspension 1200 ml of 3N aqueous sodium hydroxide solution were added with stirring until two clear phases with no solid particles were obtained. The organic phase was discarded and the aqueous phase extracted 5 times with each 1000 ml of methylene chloride. The combined organic phases were filtered and the filtrate evaporated at 50° C./16 torr. 548.6 g of 1 were obtained as slightly yellow crystals which were identical with the product obtained above.

EXAMPLE 2

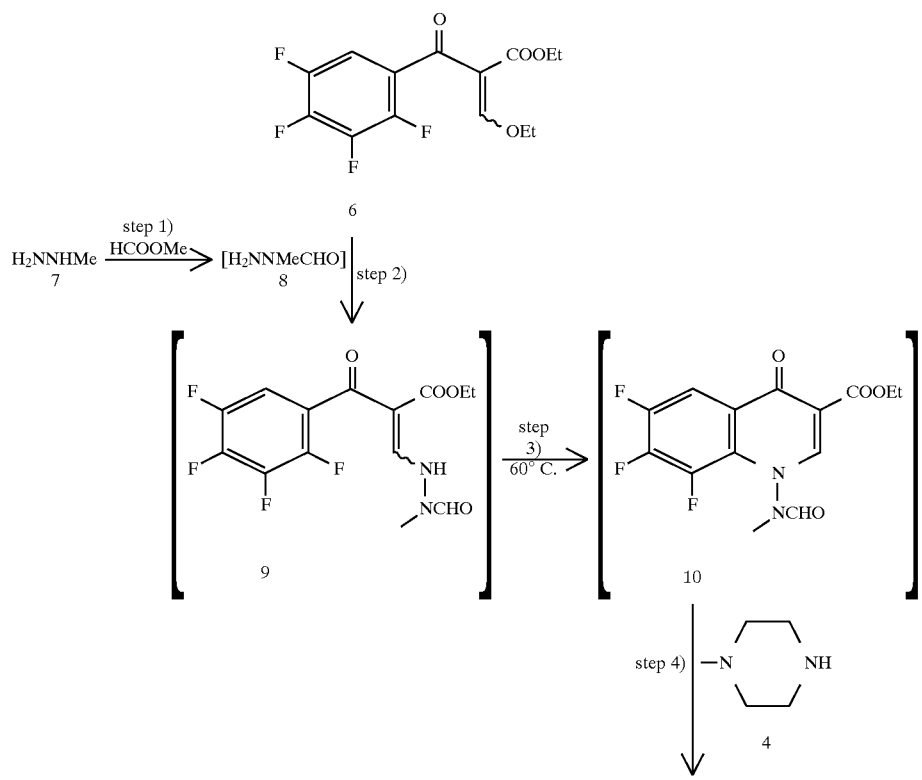

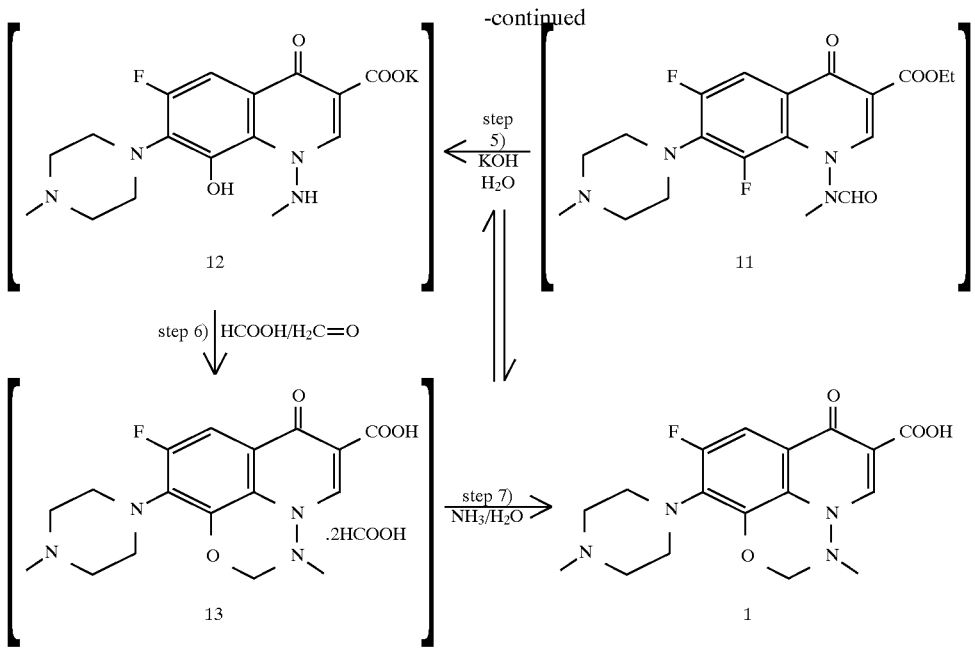

Sythesis of 9-fluoro-2,3-dihydro-3-methyl-10-(4-methyl-1-piperazinyl)-7-oxo-7H-pyrido[3,2,1-ij][4,1,2]benzoxadiazine-6-carboxylic acid (1)

Step 1) Preparation of N-amino-N-methylformamide (8)

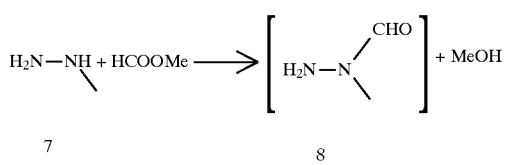

In a 100 ml 2 necked round bottom flask equipped with a magnetic stirrer, a 50 ml dropping funnel, a thermometer and an inert gas supply 23.0 g of methylhydrazine (7, 500 mmol) were treated under argon with stirring and cooling in an ice bath with 30.8 g of methyl formate (513 mmol) over 45 minutes keeping the temperature in the range of 10°–15° C. The pale yellow reaction mixture was stirred at room temperature for 3 hours to yield a solution containing the crude product 8 which was directly used for step 2).

Step 2) &
Step 3) Preparation of ethyl 6,7,8-trifluoro-1,4-dihydro-1-(N-methyl-formamido)-4-oxo-3-quinolinecarboxylate (10)

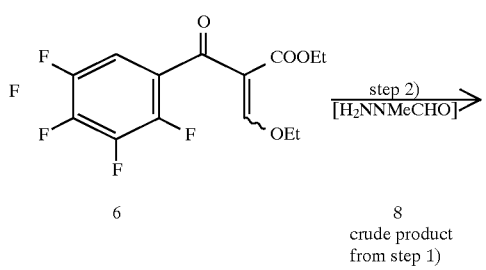

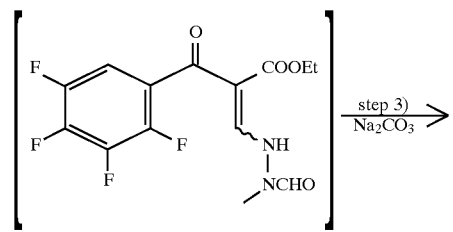

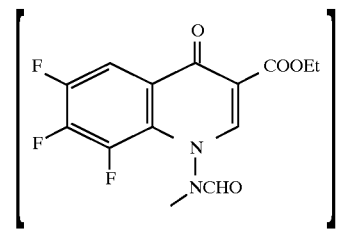

In a 1 liter 4-necked round bottom flask equipped with a mechanical stirrer, a descending Liebig condenser, a thermometer and an inert gas supply a stirred solution of 160.12 g of ethyl 3-ethoxy-2-(2,3,4,5-tetrafluoro-benzoyl)acrylate (6, 500 mmol) in 600 ml of toluene under argon at room temperature was treated during 5 minutes with the solution of 8. prepared in step 1) whereby the temperature rose to 37° C. After the addition of 58.3 g of sodium carbonate (550 mmol) the resulting beige suspension was heated to reflux and a solvent mixture was distilled off until a b.p. of 111° C. was reached. The suspension containing crude 10 was cooled to 80° C. and directly used for step 4).

Step 4) Preparation of ethyl 6,8-difluoro-1,4-dihydro-1-(N-methylformamido)-7-(4-methyl-1-piperazinyl)-4-oxo-3-quinolinecarboxylate (11)

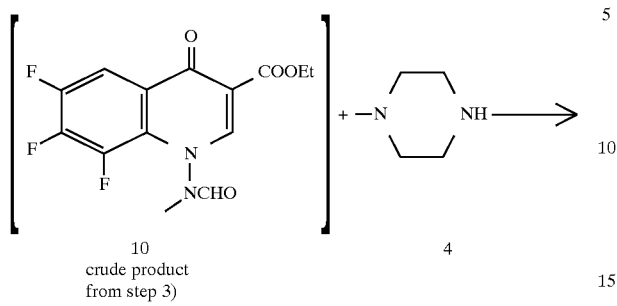

10
crude product
from step 3)

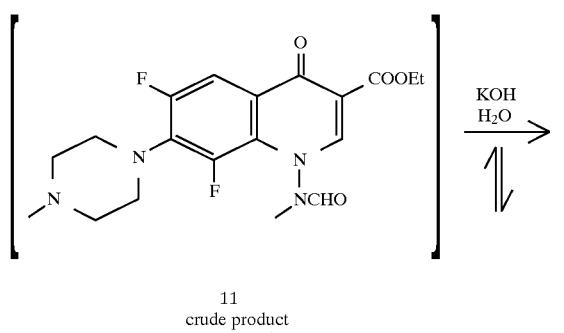

11

To the suspension of 10 in toluene obtained in step 3) was added at 80° C. with stirring 55.0 ml of N-methylpiperazine (4, d=0.902, 500 mmol), and after introduction of a Dean Stark separator the reaction mixture was heated to reflux for 6 hours, by which time ca. 11 ml of an aqueous phase separated and the temperature rose to 116° C. After cooling the brown suspension to 80° C. 9.0 ml of water (deionized, 500 mmol) was added, and after further cooling to 60°–65° C. the precipitate was filtered through a glass filter funnel, the filter cake was washed with 2 portions of 100 ml, in total 200 ml, of toluene. The combined filtrates were evaporated in a rotary evaporator at 50° C./20 torr to yield 232.0 g of a brown, partly crystalline oil containing the intermediate 11 which was directly used for step 5).

Step 5) Preparation of 6-fluoro-1,4-dihydro-8-hydroxy-1-(methylamino)-7-(4-methly-1-piperazinyl)4-oxo-3-quinolinecarboxylic acid (12)

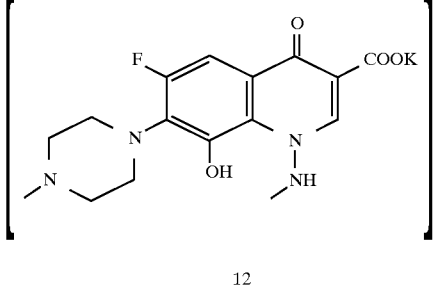

11
crude product
from step 4)

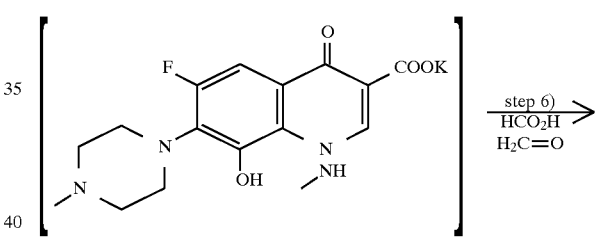

12

The crude product (232.0 g) of step 4) containing 11 was transferred to a 2 liter steel reactor equipped with a steel mechanical stirrer, a thermo-couple, a descending Liebig condenser and an inert gas supply using 1000 ml of water (deionized). To the stirred toluene/water/ethanol slurry under argon 99.0 g of potassium hydroxide (1.5 mol) were added and dissolved by heating the reactor in an oil bath. From the resulting brown solution a total of ca. 270 ml of solvent mixture was distilled off during ca. 60 minutes. At 90° C. a solution of 231.0 g of potassium hydroxide (3.5 mol) in 260 ml of water (deionized) was added, and the reaction mixture was heated during 96 hours at 105° C. The dark brown reaction mixture containing 12 was cooled to room temperature and directly used for step 6).

Step 6) &
Step 7) Preparation of 9-fluoro-2,3-dihydro-3-methyl-10-(4-methyl-1-piperazinyl)-7-oxo-7H-pyrido[3,2,1-ij][4,1,2]benzoxadiazine-6-carboxylic acid (1)

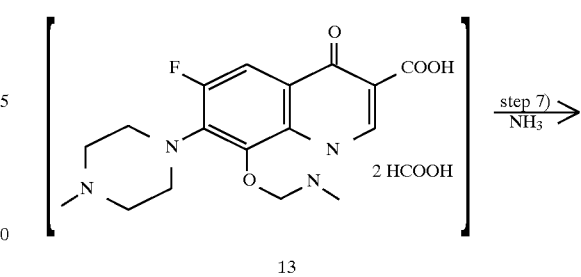

12

13

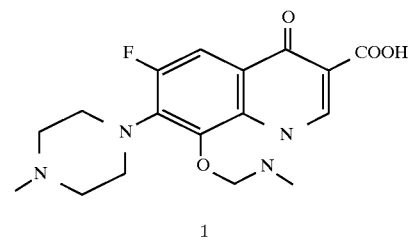

1

To the dark brown reaction mixture of step 6) containing 12 340 ml of 85% formic acid (ca. 7.5 mol) were added dropwise during 5 minutes without exceeding a temperature of 50° C. In the temperature range of 40°–50° C. 75.0 ml of aqueous 36.5% formaldehyde (ca. 1.0 mol) were added over 5 minutes and the resulting brown suspension was heated to 70° C. for 30 minutes, during which time gas evolution occurred. After cooling to 5°–10° C. 300 ml of 25% aqueous ammonia (ca. 4 mol) were added and the resulting black solution was stirred for 30 minutes. To this solution 9 g of activated charcoal were added and the resulting black suspension was stirred for 15 minutes and filtered through a glass fibre filter. The filtrate was extracted with 5 portions of 1000 ml, in total 5000 ml, of methylene chloride. The combined extracts were filtered through a glass fibre filter to remove small amounts of insoluble by-products, and the dark brown filtrate was evaporated in a rotary evaporator at 50° C./20 torr to dryness to yield 107.6 g of brown crystals. The crystals were taken up in 400 ml of ethanol and the resulting slurry was stirred for 1 hour at 0°–5° C., filtered, and the filter cake was washed with 100 ml of ethanol to yield after drying at 50° C./35 torr overnight 83.7 g of crude 1 as yellow crystals. This crude material was suspended in a mixture of 835 ml of ethanol, 415 ml of toluene and 415 ml of water (deionized) and heated to reflux. From the clear yellow solution formed 835 ml of solvent mixture was distilled off, whereby the temperature rose from 74°–78° C., and a yellow precipitate was formed. The suspension was cooled to room temperature, stirred for 1 hour, filtered, and the filter cake was washed with 3 portions of 60 ml, in total 180 ml, of ethanol to yield after drying at 50° C./35 torr overnight as the product 77.71 g (43% relative, to 6) of 1 as yellow crystals of m.p. 265°–268° C. (dec.).

EXAMPLE 3

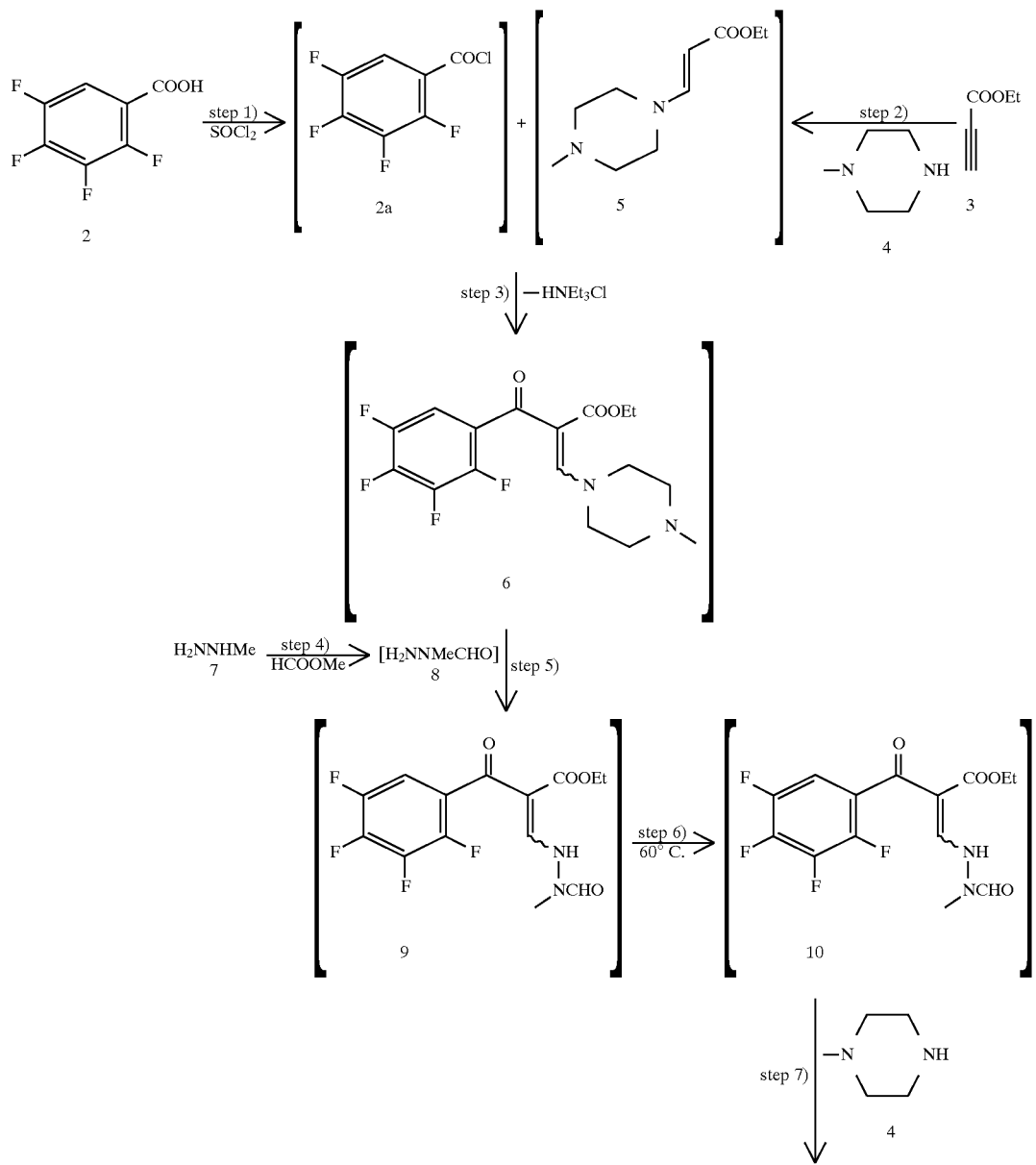

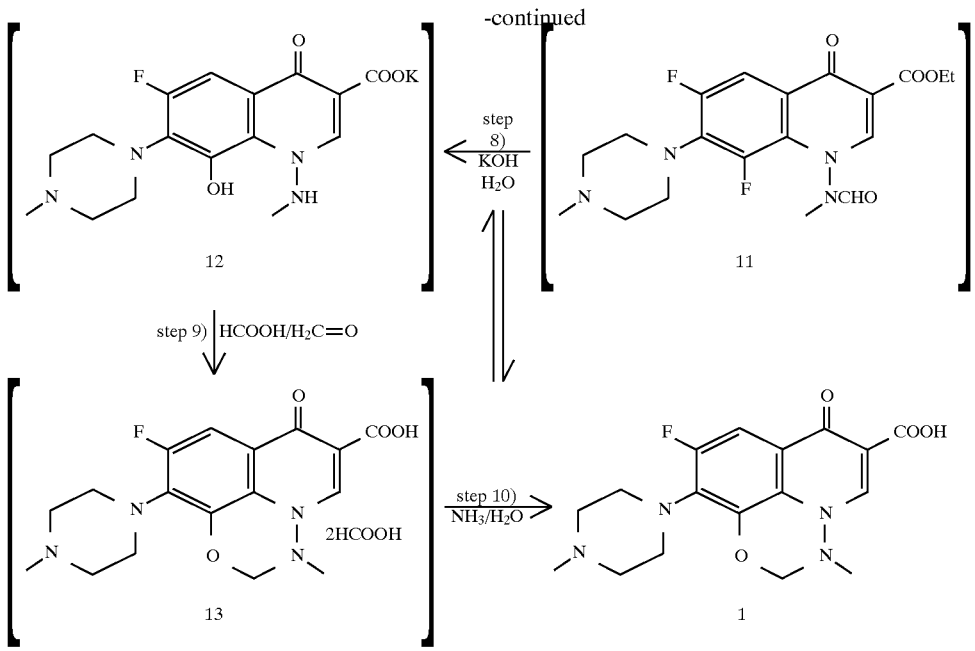

Synthesis of 9-fluoro-2,3-dihydro-3-methyl-10-(4-methyl-1-piperazinyl)-7-oxo-7H-pyrido[3,2,1-ij][4,1,2]benzoxadiazine-6-carboxylic acid (1)

Step 1) Preparation of 2,3,4,5-tetrafluorobenzoic acid chloride (2a)

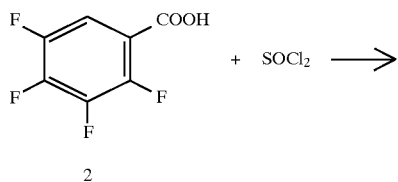

In a 500 ml round bottom flask equipped with a magnetic stirrer, a reflux condenser and an inert gas supply 97.05 g of 2,3,4,5-tetrafluorobenzoic acid (2, 500 mmol) were suspended under argon and with stirring in 100 ml of n-hexane and 0.5 ml of N,N-dimethyl formamide. To this suspension 44 ml of thionyl chloride (d=1.64, 600 mmol) were added at room temperature, and the mixture was heated to reflux for 15 hours. The light yellowish solution was evaporated in a rotary evaporator at 50° C. reducing the pressure first to 200 torr until distillation ceased, then to 30 torr holding this pressure for 3 minutes to yield 107.1 g of the crude acid chloride 2a as a pale yellow liquid, which was kept under argon and directly used for step 3).

Step 2) Preparation of ethyl 3-(4-methylpiperazinyl)acrylate (5) (cis/trans-mixture)

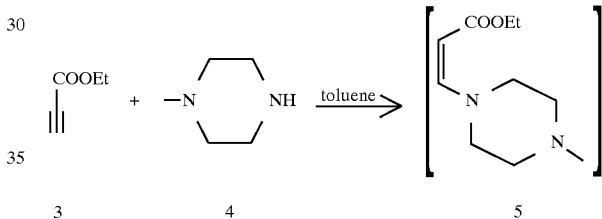

In a 1.5 liter 4 necked round bottom flask equipped with a mechanical stirrer, a reflux condenser, a 100 ml dropping funnel, a thermometer and an inert gas supply a solution of 51.8 ml of ethyl propionate (3, d=0.965, 510 mmol) under argon in 300 ml of toluene was treated dropwise with 55.0 ml of N-methylpiperazine (4, d=0.902, 500 mmol) during ca. 90 minutes without exceeding 50° C. The yellow solution containing 5 was directly used for step 3).

5 (or its methyl analogue) can also be prepared as follows:

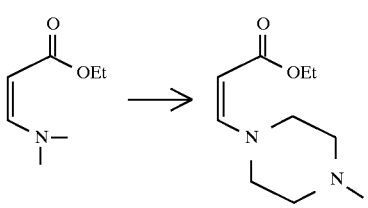

A mixture of 7.16 g (50 mmol) of ethyl (3-dimethylamino)acrylate and 5.83 ml (52.5 mmol) of 1-methylpiperazine was heated in a 25 ml 3-necked round bottom flask with stirring and a constant stream of argon in an oil bath at 155° C. until the reaction mixture reached a temperature of 150° C. After cooling to room temperature, the product (9.60 g, 97.8%), obtained as a brown oil, was used without further purification.

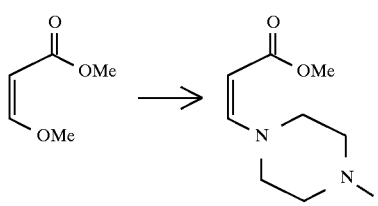

Step 4) Preparation of N-amino-N-methylformamide (8)

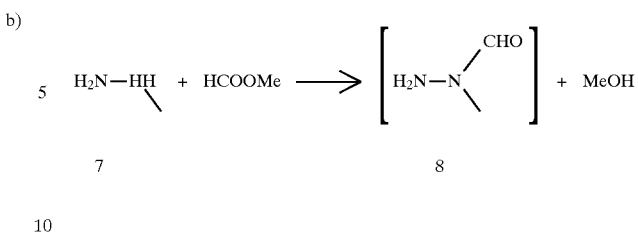

A mixture of 5.80 g (50 mmol) of methyl (3-methoxy) acrylate and 5.83 ml (52.5 mmol) of 1-methylpiperazine in a 25 ml 3-necked round bottom flask equipped with a Dean-Stark-separator was heated with stirring in an oil bath at 150° C. for 2 hours, during which time the temperature of the reaction mixture rose to 140° C. After cooling to room temperature, the product (9.25 g, 93%), obtained as a yellow oil, was used without further purification.

Step 3) Preparation of ethyl 3-(4-methylpiperazinyl)-2-(2,3,4,5-tetrafluorobenzoyl)acrylate (6)

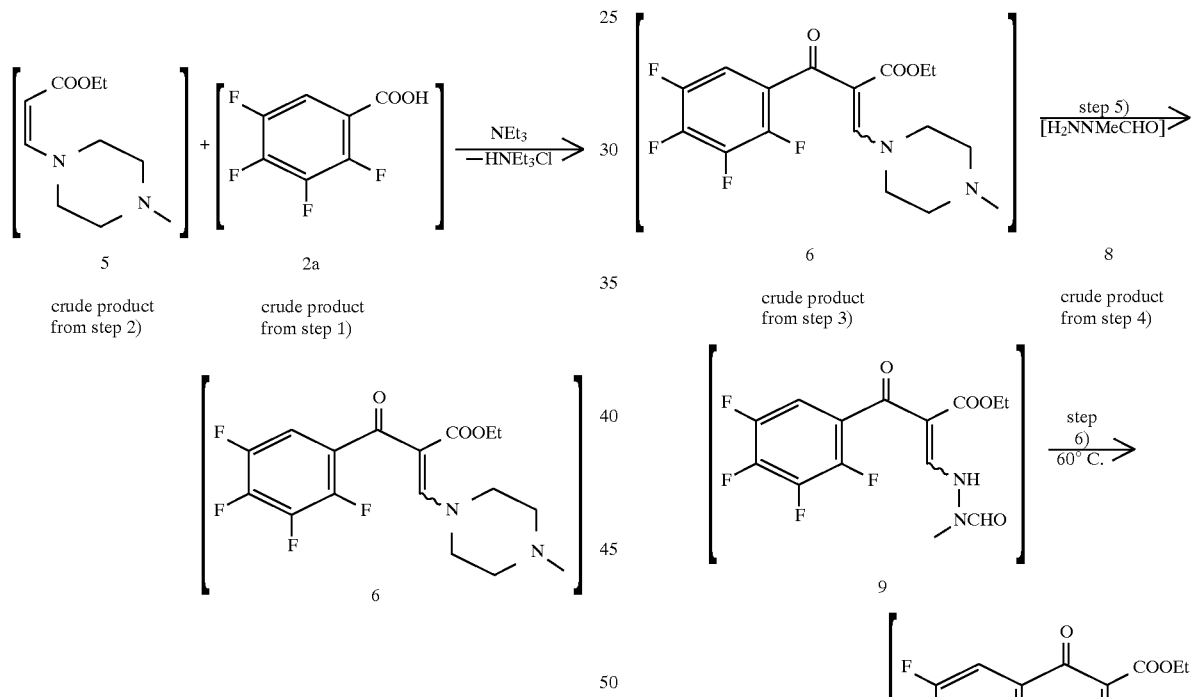

To the yellow solution of 5 obtained in step 2) was added at room temperature under argon with stirring 130 ml of toluene and 70 ml of triethyl amine (d=0.726, 500 mmol), and the mixture was heated to reflux. At reflux temperature (111° C.) a solution of the acid chloride 2a prepared in step 1) and dissolved in 100 ml of toluene was added dropwise over 30 minutes, and the resulting black suspension was kept at reflux for 30 minutes. The reaction mixture was allowed to cool to 60°–65° C. and filtered through a glass filter funnel with intense suction. The filter cake was washed with 2 portions of 100 ml, in total 200 ml, of toluene and the combined filtrates containing 6 were directly used for step 5).

In a 100 ml 2-necked round bottom flask equipped with a magnetic stirrer, a 50 ml dropping funnel, a thermometer and inert gas supply 23.0 g 10 of methylhydrazine (7, 500 mmol) were treated under argon with stirring and cooling in an ice bath dropwise with 30.8 g of methyl formate (513 mmol) over 45 minutes keeping the temperature in the range of 10°–15° C. The pale yellow reaction mixture was stirred at room temperature for 3 hours to yield a solution containing the crude product 8, which was directly used for step 5).

Step 5) &
Step 6) Preparation of ethyl 6,7,8-trifluoro-1,4-dihydro-1-(N-methyl-formamido)-4-oxo-3-quinolinecarboxylate (10)

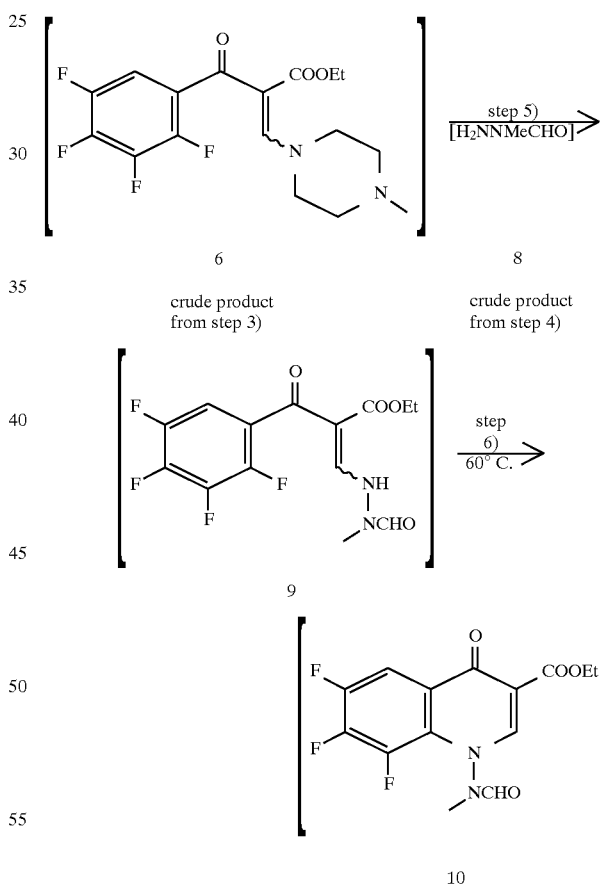

To the stirred, black solution of 6 obtained in step 3) was added with stirring at 60°–65° C. 58.3 g of sodium carbonate (550 mmol). To the resulting dark brown suspension the solution of obtained in step 4) was added over 5 minutes, and the reaction mixture was kept with stirring at 60°–65° C. for 2 hours. The resulting dark brown suspension containing crude 10 was directly used for step 7).

Step 7) Preparation of ethyl 6,8-difluoro-1,4-dihydro-1-(N-methylformamido)-7-(4-methyl-1-pipierazinyl)-4-oxo-3-quinolinecarboxylate (11)

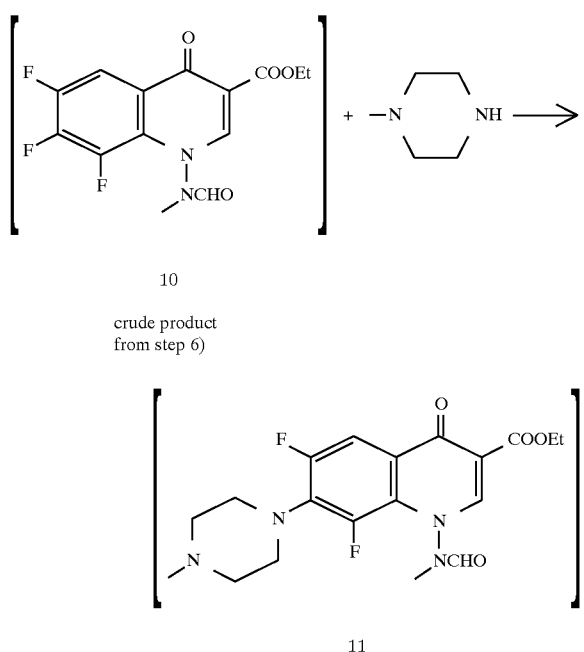

To the suspension of 10 in toluene obtained in step 6) was added at 60°–65° C. with stirring 55.0 ml of N-methylpiperazine (4, d=0.902, 500 mmol), and after introduction of a Dean Stark separator the reaction mixture was heated to reflux for 6 hours, by which time ca. 30 ml of an aqueous phase separated and the temperature rose to 116° C. After cooling to 80° C. 9.0 ml of water (deionized, 500 mmol) was added and after further cooling to 60°–65° C. the precipitation was filtered through a glass filter funnel, the filter cake was washed with 2 portions of 100 ml, in total 200 ml, of toluene. The combined filtrates were evaporated in a rotary evaporator at 50° C./20 torr to yield 264.8 g of a brown, partly crystalline oil containing the intermediate 11, which was directly used for step 8).

Step 8) Preparation of 6-fluoro-1,4-dihydro-8-hydroxy-1-(methylamino)-7-(4-methyl-1-piperazinyl)-4-oxo-3-quinolinecarboxylic acid (13)

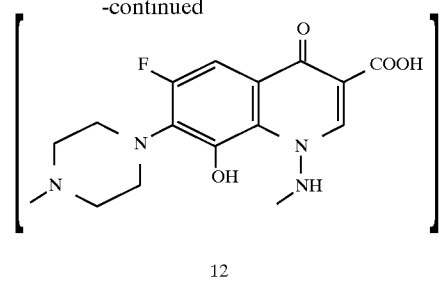

The crude product (264.8 g) of step 7) containing 11 was transferred to a 2 liter steel reactor equipped with a steel mechanical stirrer, a thermo-couple, a descending Liebig condenser and an inert gas supply using 1000 ml of water (deionized). To the stirred slurry under argon 99.0 g of potassium hydroxide (1.5 mol) were added and dissolved by heating the reactor in an oil bath. From the resulting brown solution a total of ca. 300 ml of a toluene/ethanol/water mixture was distilled off during ca. 60 minutes. At 95° C. a solution of 231.0 g of potassium hydroxide (3.5 mol) in 260 ml of water (deionized) was added, and the reaction mixture was heated during 72 hours at 105° C. The dark brown reaction mixture containing 12 was cooled to room temperature and directly used for step 10).

Step 9) & Step 10) Preparation of 9-fluoro-2,3-dihydro-3-methyl-10-(4-methyl-1-piperazinyl)-7-oxo-7H-pyrido[3,2,1-ij][4,1,2]benzoxadiazine-6-carboxylic

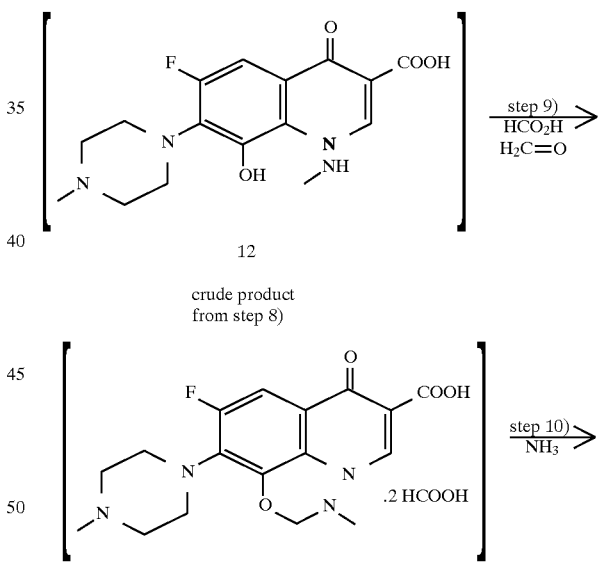

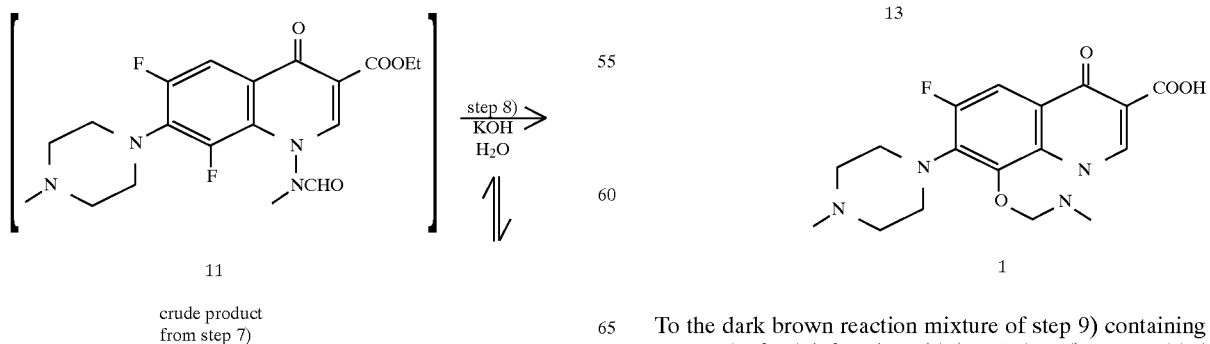

To the dark brown reaction mixture of step 9) containing 12 340 ml of 85% formic acid (ca. 7.5 mol) were added dropwise during 5 minutes without exceeding a temperature of 50° C. In the temperature range of 40°–45° C. 75.0 ml of aqueous 36.5% formaldehyde (ca. 1.0 mol) were added over 5 minutes and the resulting brown suspension was heated to 70° C. for 30 minutes, during which time gas evolution occurred. After cooling to 5°–10° C. 300 ml of 25% aqueous ammonia (ca. 4 mol) were added and the resulting black solution was stirred for 30 minutes. To this solution 9 g of activated charcoal were added, and the resulting black suspension was stirred for 15 minutes and filtered through a glass fibre filter. The filtrate was extracted with 5 portions of 1000 ml, in total 5000 ml, of methylene chloride. The combined extracts were filtered through a glass fibre filter to remove small amounts of insoluble by-products, and the dark brown filtrate was evaporated in a rotary evaporator at 50° C./20 torr to dryness to yield 100.7 g of brown crystals. The crystals were taken up in 400 ml of ethanol and the resulting slurry was stirred for 1 hour at 0°–5° C., filtered, and the filter cake was washed with 100 ml of ethanol to yield after drying at 50° C./30 mbar overnight 67.3 g of crude 1 as yellow crystals. This crude material was suspended in a mixture of 670 ml of ethanol, 335 ml of toluene and 335 ml of water (deionized) and heated to reflux. From the clear yellow solution formed 670 ml of a solvent mixture was distilled off whereby the temperature rose from 72°–79° C. and a yellow precipitation was formed. The suspension was cooled to room temperature, stirred for 1 hour, filtered, and the filter cake was washed with 3 portions of 60 ml, in total with 180 ml of ethanol to yield after drying at 50° C./30 mbar overnight as the product 60.40 g (33% relative to 2) as yellow crystals of m.p. 261°–265° C. (dec.).

EXAMPLE 4 temperature of 30° C. The yellow, slightly opaque solution was evaporated at 50° C./30 torr until constant weight. 91.8 g of 3-(benzylmethyl-amino)acrylic acid ethyl ester were obtained as a yellow oil which was further used without purification.

Synthesis of 6,7,8-trifluoro-1,4-dihydro-1-(N-methylformamido)-4-oxo-3-quinoline-carboxylic acid ethyl ester a) via 3-(benzylmethylamino)-2-(2,3,4,5-tetrafluorobenzoyl)acrylic acid ethyl ester A solution of 21.3 g (100 miol) of the 3-(benzylmethylamino)acrylic acid ethyl ester previously obtained and 10.7 g (106 mmol) of triethylamine in 40 ml of toluene were heated to 100° C. With stirring and reflux a solution of 21.3 g (100 mmol) of 2,3,4,5-tetrafluorobenzoic acid chloride in 100 ml of toluene were added dropwise, in the course of which the temperature rose to 114° C., and a precipitate was formed. The hot suspension was filtered and the filter residue washed 3 times with 50 ml of toluene. The combined filtrates containing the 3-(benzylmethylamino)-2-(2,3,4,5-tetrafluorobenzoyl)acrylic acid ethyl ester 80 formed were stirred over-night at room temperature with 7.41 g (100 mmol) of N-amino-N-methylformamide, and the brown suspension obtained was evaporated under reduced pressure. The brown crystal mass was taken up in 400 ml of dichloromethane, extracted with 2 portions of 180 and 70 ml of 1N aqueous hydrochloric acid, the organic phase dried over magenisum sulphate, ifitered and evaporated at 45° C./55 torr. The rust-brown, sticky residue (39.5 g) was suspended in 10 ml of tert.-butylmethyl ether, digested

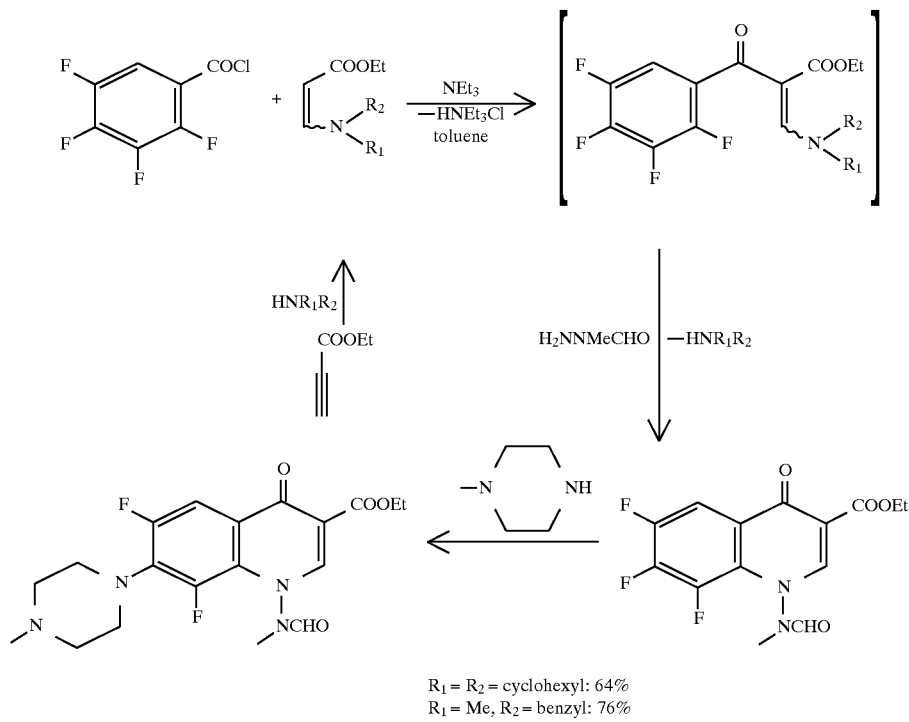

$R_1 = R_2$ = cyclohexyl: 64%
$R_1$ = Me, $R_2$ = benzyl: 76%

Synthesis of 3-(benzylmethylamino)acrylic acid ethyl ester

With stirring and cooling a solution of 48.5 g (0.4 mol) of N-benzyl-N-methyl-amine was added dropwise to a solution of 39.2 g (0.4 mol) of propiolic acid ethyl ester in 200 ml of toluene in the course of 20 min. so as not to exceed a intensely for 30 min., the crystals filtered, washed twice with each 50 ml of tert.-butylmethyl ether and dried at 50° C./33 torr. 24.8 g (76%) of 3-(2-formyl-2-methylhydrazino)-2-(2,3,4,5-tetrafluorobenzoyl)acrylic acid ethyl ester were obtained as a white powder of mp 192° C.

b) via 3-(dicyclohexylamino)-2-(2,3,4,5-tetrafluorobenzoyl)acrylic acid ethyl ester A solution of 1.81 g (10 mmol) of dicyclohexylamine was added to a solution of 0.98 g (10 mmol) of propiolic acid ethyl ester in 4 ml of toluene, and the mixture was stirred for 6 hours at room temperature. The resulting yellow solution of 3-(dicyclohexylamino) acrylic acid ethyl ester was heated to 100° C., 0.98 g (9.6 mmol) of triethylaimine were added and the mixture heated to reflux. With stirring a solution of 1.93 g (9.1 mmol) of 2,3,4,5-tetrafluorobenzoic acid chloride in 10 ml of toluene was added in the course of 10 min. The brown suspension was filtered hot and the filter residue washed twice with 15 ml of toluene. The united filtrates containing the so formed 3-(dicyclohexyl-amino)-2-(2,3,4,5-tetrafluorobenzoyl)acrylic acid ethyl ester were stirred for 160 hours at room temperature with 7.41 g (100 mmol) of N-amino-N-methylformamide. The resulting brown suspension was dissolved in 200 ml of dichloromethane, extracted with 50 ml of 1N aqueous hydrochloric acid, and the aqueous extracts washed twice with each 50 ml of dichloromethane. The organic phases were united, dried over magnesium sulphate, filtered and evaporated at 45° C./30 torr. The light-brown, oily residue (4.65 g) was suspended in 10 ml of tert.-butyl methyl ether, digested intensely for 30 min., the crystals filtered, washed twice with each 5 ml of tert.-butyl methyl ether and dried at 25° C./33 torr. There were obtained 1.91 g (64%) of 3-(2-formyl-2-methylhydrazino)-2-(2,3,4,5-tetrafluorobenzoyl)acrylic acid ethyl ester as a white powder of mp 189°.

Sythesis of 6,8-Difluoro-1,4-dihydro-1-(N-methylformamido)-7-(4-methyl- 1-piuerazinyl )-4-oxo-3-quinoline-carboxylic acid ethyl ester A suspension of 4.92 g (15 mmol) of 3-(2-formyl-2-methylhydrazino)-2-(2,3,4,5-tetrafluorobenzoyl)acrylic acid ethyl ester and 3.41 ml (30.1 mmol) of N-methyl-piperazine in 15 ml of toluene were heated at reflux for 7.5 hours after which a clear, yellow solution was formed. After the addition of further 2.08 ml of N-methyl-piperazine the mixture was heated for 2 hours, cooled and evaporated at 49° C./130 torr. The yellowish oil (13.7 g) was taken up in 30 ml of dichloromethane, washed with 50 ml of water and subsequently twice with each 7.5 ml of half-saturated brine. The aqueous extracts were washed twice with each 15 ml of dichlormethane, the organic phases united, dried over magnesium sulphate, filtered and evaporated at 47° C./20 torr. The crystalline, beige residue (6.1 g) was suspended in 40 ml of tert.-butylmethyl ether, vigorously digested for 50 min., the crystals filtered, washed twice with each 10 ml of tert.-butylmethyl ether and dried at 45° C./13 torr. 5.41 g (88%) of 6,8-difluoro-1,4-dihydro-1-(N-methylformamido) 7-(4-methyl- 1-piperazinyl)-4-oxo-3-quinoline-carboxylic acid ethyl ester were obtained as beige crystals of mp 180° C.

EXAMPLE 5

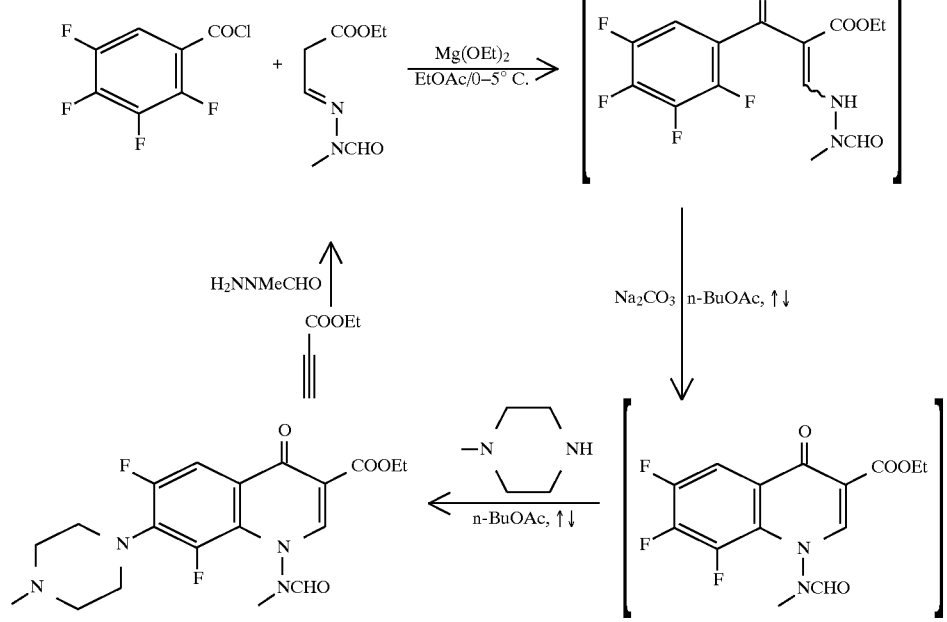

Synthesis of 3-(formylmethylhydrazono)-propionic acid ethyl ester 39.24 g (0.4 mol) of propiolic acid ethyl ester were added to a solution of 29.63 g (0.4 mol) of N-amino-N-methylformamide in 80 ml of dioxane and left standing for 3 weeks at room temperature. The yellow solution was evaporated at 40° C./30 torr and the residue filtered over a silical gel column (350 g) with a mixture of dichloromethane/n-hexane 49:1 in fractions of 250 ml each. Fractions 2 to 10 were united and evaporated at 40° C./30 torr, yielding 63.9 g (93%) of 3-(formylmethylhydrazono)-propionic acid ethyl ester as a yellow fluid (IR: 3462, 2984, 1735, 1688, 1629, 1183, 1045 cm$^{-1}$).

Synthesis of 6,8-difluoro-1,4-dihydro-1-(N-methylformamido)-7-(4-methyi-1-piperazinyl)-4-oxo-3-quinoline-carboxylic acid ethyl ester A yellow suspension of 8.61 g (50 mmol) of 3-(formylmethylhydrazono)-propionic acid ethyl ester and 5.72 g (50 mmol) of magnesium ethylate in 30 ml of ethyl acetate were heated at reflux for 65 min. The solution was cooled to 0°–5° C., and at this temperature a solution of 10.63 g (50 mmol) of 2,3,4,5-tetra-fluoro-benzoic acid chloride in 10 ml of ethyl acetate was added dropwise in the course of 20 min. Subsequently the suspension was stirred for 30 min. in the cold and afterwards for 18.5 hours at room temperature. After the addition of a solution of 7.0 ml of 85% formic acid in 50 ml of water the mixture was well mixed and the two phases separated. The aqueous phase was extracted twice with each 50 ml of ethyl acetate, the united organic phases dried over sodium sulphate, filtered and evaporated at 50° C./20 torr. The residue of 3-(2-formyl-2-methyl-hydrazino)-2-(2,3,4,5-tetrafluorobenzoyl)acrylic acid ethyl ester (18.81 g) was dissolved in 55 ml of butyl acetate, 5.83 g (55 nmol) of sodium carbonate were added, and the mixture was heated with stirring for 25 min. at reflux. 11.1 ml (100 mmol) of N-methylpiperazine were added to the resulting suspension of 3-(2-formyl-2-methyl-hydrazino)-2-(2,3,4,5-tetrafluorobenzoyl)acrylic acid ethyl ester and heated for 4.5 hours under reflux using a water trap, in the course of which the temperature rose from 114° to 125° C. The suspension was evaporated at 50° C./20 torr and the resulting brown residue (31.8 g) worked up in analogy to Example 3 resulting in 10.2 g (50%) of 6.8-difluoro-1,4-dihydro-1-(N-methylformamido)-7-(4-methyl-1-piperazinyl)-4-oxo-3-quinoline-carboxylic acid ethyl ester as yellowish crystals of mp 178° C.

EXAMPLE 6
Synthesis of N-amino-N-methylformamide (3)

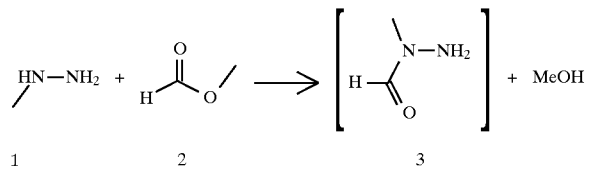

In a 1000 ml three-neck flask with thermometer, reflux condenser, mechanical stirrer and inert gas supply 91.6 g of methylhydrazine (1; 1.9 mol) were cooled in an argon atmosphere and, with stirring, 120.3 g of formic acid methyl ester (2, 1.9 mol) were added within 90 min. at 0°–5° C. After further 6 hours of stirring at 0°–5° C. the mixture was heated to room temperature. 211.9 g of N-amino-N-methylformamide were obtained as a colourless fluid. This product contains (apart from methanol) about 10 mol % of N-(methylamino)-formamide (3). The methanol was not distilled off, i.e. the crude product was used directly.

Synthesis of 2-(sodium-formyl)acetic acid ethyl ester (6)

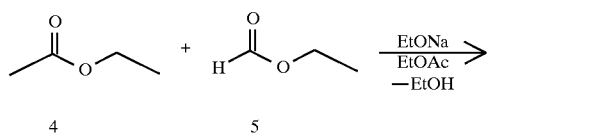

In a 1000 ml three-neck flask with thermometer, reflux condenser, mechanical stirrer and inert gas supply 68.05 g of sodium ethanolate (1.00 mol) were added in an argon atmosphere with intense stirring to a solution of 74.08 g of formic acid ethyl ester (5; 1.00 mol) in 350 ml of ethyl acetate (4; 1.00 mol) at 0°–5° C. The mixture was stirred 2.5 hours at this temperature. After the addition of 150 ml of ethyl acetate (4) the mixture was stirred for 13.5 hours at 0°–5° C., heated to room temperature and centrifuged for 10 min. at 4000 rpm. The decanted solution was evaporated at 40° C./190 torr to about 150 ml and centrifuged anew. The collected centrifugates were dried for 3 hours at 45° C./40 torr. 100.0 g of 2-(sodium-formyl)acetic acid ethyl ester (6) were obtained as a white powder of mp 183°–186° C. (dec.).

Sythesis of 3-(N-formylmethylhydrazono)-propionic acid ethyl ester (7)

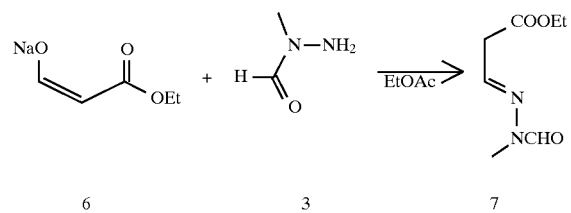

In a 200 ml four-neck flask with 50 ml dropping funnel, thermometer, magnetic stirrer and inert gas supply, in an argon atmosphere and with stirring 4.35 g of glacial acetic acid (72.4 imnol) were added to 5.36 g of the above obtained N-amino-N-methylformamide in 30 ml of deionized water. At 0°–5° C. an intensely stirred suspension of 9.00 g of 2-(sodium-formyl)acetic acid ethyl ester (6; 65.1 mmol) in 40 ml of ethyl acetate were added in the course of 60 min. The reaction mixture was stirred for 4 hours at 0°–5° C. The phases were separated and the aqueous phase extracted once with 30 ml of ethyl acetate. The united organic extracts were washed once with 20 ml of deionized water, dried over 4 g of sodium sulphate and evaporated to dryness at 40° C./40 torr. 8.81 g of 3-(N-formylmethyl-hydrazono)-propionic acid ethyl ester (7) were obtained as an orange-red liquid.

Synthesis of 2,3,4,5-tetrafluorobenzoic acid chloride (9)

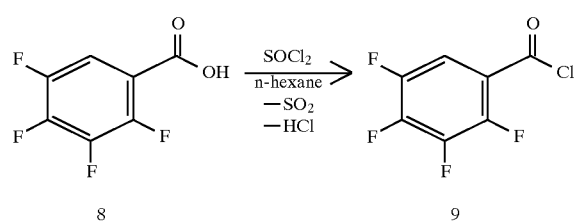

In a 1000 ml three-neck flask with thermometer, reflux condenser, 50 ml dropping funnel, mechanical stirrer, bubble counter, exhaust pipe and oil bath 0.5 ml of dimethylformamide were added with stirring to a suspension of 97.05 g of 2,3,4,5-tetrafluorbenzoic acid (8; 0.5 mol) in 100 ml of n-hexane. In the course of 10 min. 44 ml of thionyl chloride (0.61 mol) were added, and the reaction mixture was heated for 17 hours at reflux temperature. After cooling to room temperature, the n-hexane was evaporated off at 55° C. and increasing vacuum for 30 min. (at the end 3 min. at 55° C./40 torr). 104.8 g of 2,3,4,5-tetrafluoro-benzoic acid chloride (9) were obtained as a yellow, clear liquid, which was directly used in the next step.

Sythesis of 2-(2,3,4,5-tetrafluorobenzoyl)-3-(2-methyl-2-formamidohydrazinyl)-acrylic acid ethyl ester (10)

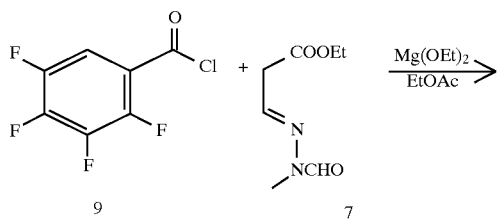

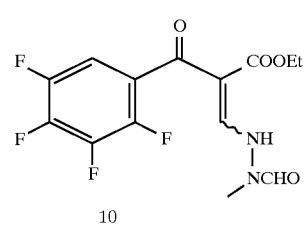

In a 250 ml three-neck flask with reflux condenser, oil bath, magnetic stirrer, thermometer, 25 ml dropping finnel and inert gas supply, in an argon atmosphere 8.61 g 3-(N-formylmethylhydrazono)-propionic acid ethyl ester (7; 50 mmol) was dissolved at room temperature in 30 ml of ethyl acetate and, with stirring, 5.70 g magnesium ethanolate (50 mmol) were added. The yellow suspension was heated at reflux temperature for 3 hours, a yellow-orange solution being formed. Subsequently the mixture was cooled to 0°–5° C., whereupon in the course of 35 min. a solution of 10.63 g of tetrafluorobenzoic acid chloride (9; 50 mmol) in 10 ml of ethyl acetate were added dropwise. After stirring for 30 min. at 0°–5° C., the reaction mixture was heated to room temperature and stirred for further 15 hours. A yellow, heavily stirrable suspension was formed, which, after the addition of a solution of 7 ml of formic acid (85%, 150 mmol) in 50 ml of deionized water, turned clear. The phases were separated and the aqueous phase extracted 3 times with each 30 ml, totally 90 ml, of ethyl acetate. The united organic extracts were dried over 5 g of sodium sulphate, and the solvent was evaporated at 40° C./190 torr. 17.9 of 2-(2,3,4,5-tetrafluorobenzoyl)-3-(2-methyl-2-formamidohydrazinyl)-acrylic acid ethyl ester (10) was formed as a brownish oil.

Sythesis of 6,7,8-trifluoro-1,4-dihydro-1-(N-methylformamido)-4-oxo-3-quinoline carboxylic acid ethyl ester (11)

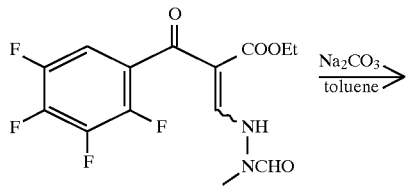

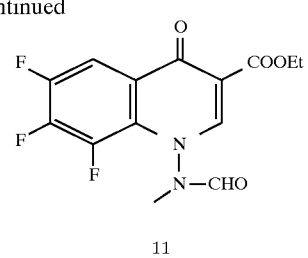

In a 200 ml four-neck flask with reflux condenser, thermometer, water trap, oil bath and inert gas supply, in an argon atmosphere 17.4 g of 2-(2,3,4,5-tetrafluorobenzoyl)-3-(2-methyl-2-formamidohydrazinyl)-acrylic acid ethyl ester (10; 50 mmol) were dissolved in 70 ml of toluene. With stirring 2.9 g of sodium carbonate (25 mmol) were added. After heating to reflux for 1.5 hours the toluene was distilled of 40° C./40 torr. The residual crystalline slurry was taken up in 100 ml of methylene chloride and 250 ml of deionized water, intensely shaken, the phases separated and the aqueous phase extracted 3 times with each 30 ml, totally 90 ml, of methylene chloride. The united organic extracts were dried over 10 g sodium sulphate and evaporated at 40° C./40 torr. The brown oily residue (25.0 g) was dissolved in 130 ml of ethanol with heating. Crystallization was started by slow stirring after removal of the heating source (about 0.5 hours) and terminated by ice/water cooling after 3 hours. The resulting crystals were filtered off and dried for 15 hours at 50° C./40 torr. 10.4 g of 6,7,8-trifluoro-1,4-dihydro-1-(N-methylformamido)-4-oxo-3-quinoline carboxylic acid ethyl ester (11) were formed as white-beige crystals of mp 190°–191° C.

EXAMPLE 7

Sythesis of 6,7,8-trifluoro-1,4-dihydro-1-(N-methylformamido)-4-oxo-3-quinoline carboxylic acid ethyl ester (11) starting from 2,3,4,5-tetrafluorobenzoic acid chloride (9)

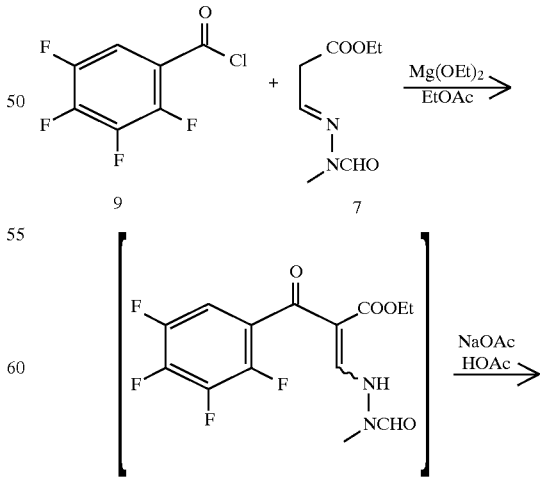

-continued

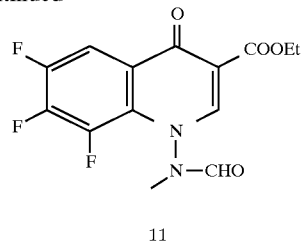

11

In a 350 ml four-neck flask with thermometer, 25 ml dropping funnel, magnetic stirrer, oil bath and inert gas supply, in an argon atmosphere 8.61 g of 3-(N-formylmethylhydrazono)-propionic acid ethyl ester (7; 50 mmol; obtained as above) were dissolved in 30 ml of ethyl acetate, whereupon 5.7 g of magnesium ethanolate (50 minol) were added. The resulting suspension was heated to reflux for 3 hours, cooled to 0° C., and at 0°–5° C. a solution of 10.63 g of 2,3,4,5-tetrafluorobenzoic acid chloride (9; 50 mmol; obtained as above) in 10 ml of ethyl acetate were added. The reaction mixture was stirred for 30 min. at 0° C. and, after removal of the cooling bath, a further 16 hours at room temperature. To the yellow-orange suspension 3.0 g of glacial acetic acid (50 mmol) and a suspension of 4.1 g of sodium acetate (50 mmol) in 25 ml of ethyl acetate were added, heated to reflux temperature and, while still hot, diluted with 30 ml of ethyl acetate. In the course of 6 hours under reflux conditions a viscous sediment was formed. After cooling to room temperature the solvent was evaporated off at 40° C./190 torr, the brownish oily residue taken up in 150 ml of methylene chloride and 100 ml of deionized water and acidified with 2.7 g of formic acid (85%, 50 mmol). The phases were separated and the aqueous phase extracted 3 times with each 20 ml, totally 60 ml, of methylene chloride. The united organic extracts were washed with 50 ml of deionized water, dried over 4 g of sodium sulphate and the solvent evaporated off at 40° C./40 torr. There remained 21.05 g of light brown crystals, which were digested in 20 ml of ethanol for 2 hours with ice/water cooling, filtered off and dried for 14 hours at 50° C./40 torr. 9.94 g of 6,7,8-trifluoro-1,4-dihydro-1-(N-methylformamido)-4-oxo-3-quinoline carboxylic acid ethyl ester (11) were formed as beige crystals of mp 191°–192° C.

We claim:

1. A process for preparing a compound which is a reaction product of the formula

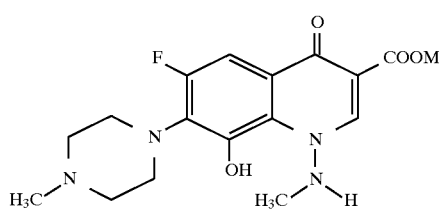

(II)

or a pharmaceutically acceptable salt thereof;
wherein M is an alkali metal cation, comprising:

reacting a compound of the formula

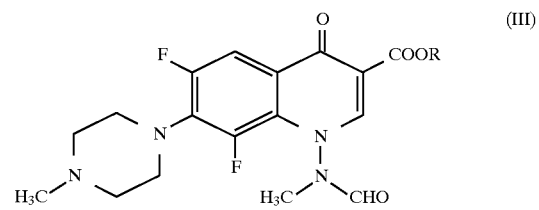

(III)

wherein R is a straight or branched chain alkyl having from one to four carbon atoms;
with an alkali metal hydroxide in an aqueous medium at a temperature of from 80° to 120° C. and a time of from 20 to 100 hours to form said reaction product of formula II.

2. A process according to claim 1, wherein the alkali metal hydroxide is potassium hydroxide.

3. A process according to claim 1, wherein R is ethyl.

4. A process according to claim 1, wherein said temperature is reflux, said time is from 70 to 100 hours, and said alkali metal hydroxide is used in an amount of at least 10 mol equivalents.

5. A process according to claim 1, wherein said alkali metal hydroxide is present in a concentration of 10 to 20% weight.

6. A process for preparing a dihydroformate of the formula

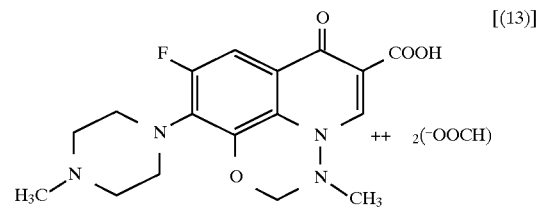

[(13)]

comprising:

cyclizing said reaction product of formula II in claim 1 with formic acid and formaldehyde to form said dihydroformate of the above formula.

7. A process according to claim 6, wherein an excess of said formic acid is added as 85% aqueous formic acid and an excess of said formaldehyde is added as 25–50% aqueous formaldehyde.

8. A process for preparing a formate of the formula

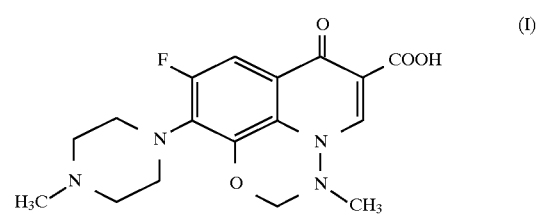

(I)

comprising:

neutralizing said dihydroformate of the formula in claim 6 with an aqueous base to form said formate of the formula I.

9. A process according to claim 8, wherein said aqueous base is aqueous ammonia.

10. A process according to claim 1 further comprising preparing said compound of formula III by:

reacting a compound of the formula

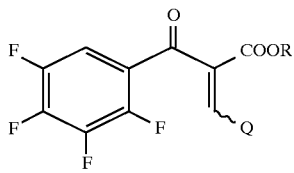
(IV)

wherein R is as previously defined in claim 1 Q is OR; N,N'-(diicycloalkyl)-amino; N-methyl-N'-benzyl-amino; or 4-methyl-piperazinyl, and the alternate bond (∿) indicates two stereospecific possibilities;

with N-amino-N-methylformamide in an inert solvent to form a resulting compound of the formula

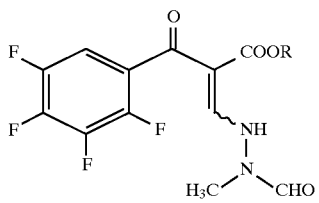
(V)

2) cyclizing said resulting compound of formula V with a base to form a quinolone of the formula

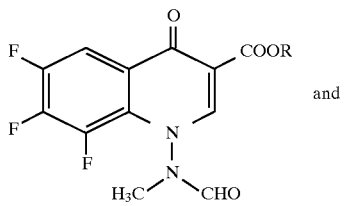
(VI)

and 3) reacting said quinolone of formula VI with N-methylpiperazine to form said compound of the formula

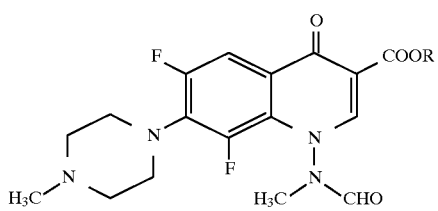
(III)

11. A process according to claim 10, wherein said inert solvent used in step a) is toluene.

12. A process according to claim 10, wherein said base used in step b) is an alkali metal carbonate.

13. A process according to claim 12, wherein said alkali metal carbonate is sodium carbonate.

14. A process according to claim 10, wherein step b) is carried out in the presence of an inert solvent at reflux temperature.

15. A process according to claim 10, wherein step c) is carried out in the presence of an inert solvent at reflux temperature.

16. A process according to claim 14, wherein said inert solvent is toluene.

17. A process according to claim 10, wherein Q is 4-methylpiperazinyl.

18. A process according to claim 10, wherein Q in formula IV is N,N'-(dicycloolkyl)-amino, N-methyl-N'-benzyl-amino or 4-methylpipararinyl, giving a compound of the formula

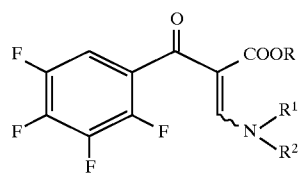
(IVb)

wherein NR$^1$R$^2$ is N, N'-(dicycloalkyl)-amino, N-methyl-N'-benzyl-amino or 4-methylpiperazinyl;

further comprising preparing said compound of formula IVb by acylating 2,3,4,5-tetrafluorobenzoic acid chloride of the formula

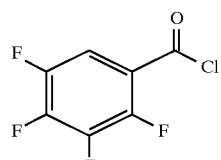
[(2a)]

with a compound of the formula

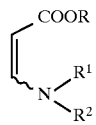
(X)

wherein NR$^1$R$^2$ is as previously defined in the presence of a base and an inert solvent.

19. A process according to claim 18, wherein NR$^1$R$^2$ is 4-methylpiperazinyl.

20. A process according to claim 18, wherein said base is a tertiary amine.

21. A process according to claim 20, wherein said tertiary amine is triethylamine.

22. A process for preparing a format compound of the formula

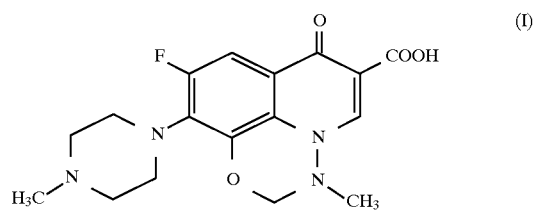
(I)

or a pharmaceutically acceptable salt thereof, comprising:

1) reacting a compound of the general structural formula

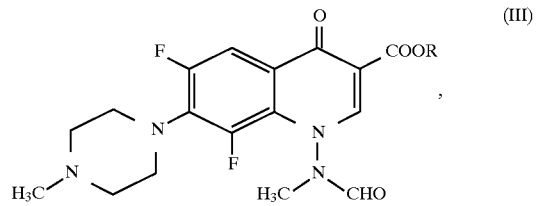
(III)

wherein R is a straight or branched chain alkyl having from one to four carbon atoms, with an alkali metal hydroxide in an aqueous medium at a temperature of from 80° to 120° C. and a time of from 20 to 100 hours to form a reaction product of the formula

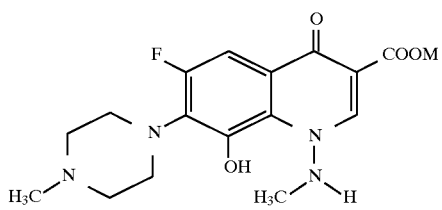 (II)

2) cyclizing said reaction product of formula with formic acid and formaldehyde to form a dihydroformate compound of the formula

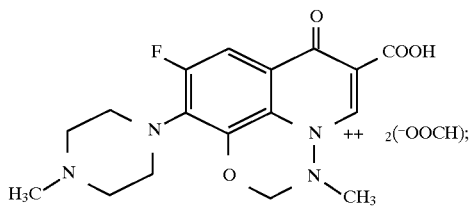 ++ $_2$(-OOCH);

and 3) neutralizing said dihydroformate compound of step 2) with an aqueous base to give solid formate compound of formula I.

23. A process according to claim 22, wherein R is ethyl.

24. A process according to claim 22, further comprising preparing said compound of formula III by:

reacting a compound of the formula

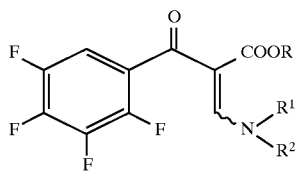 (IVb)

wherein R is as previously defined in claim 22; NR$^1$R$^2$ is N,N'-(dicycloalkyl)-amino, N-methyl-N'-benzyl-amino or 4-methyl-piperazinyl, and the alternate bond (~) indicates two stereospecific possibilities;

with N-amino-N-rnethylformamide in an inert solvent to form a resulting compound of the formula

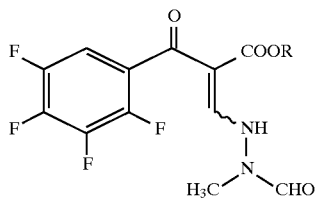 (V)

wherein R is as previously defined, 2) cycilzing said compound of formula V with a base to form a resulting compound of the formula

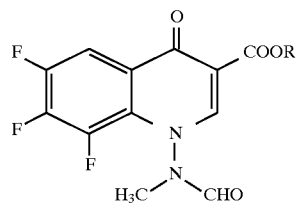 (VI)

wherein R is as previously defined; and 3) reacting said compound of formula VI with N-methylpiparazine to give said compound of the formula III.

25. A process according to claim 24, further comprising preparing said compound of formula IVb by acylating 2,3,4,5-tetrafluorobenzoic acid chloride of the formula

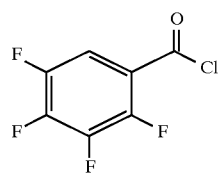

with a compound of the formula

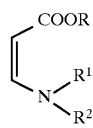 (Xa)

wherein NR$^1$R$^2$ is as previously defined in claim 18, in the presence of a base and an inert solvent.

26. A process according to claim 24, wherein NR$^1$R$^2$ is 4-methylpiperazinyl.

27. A compound of the formula

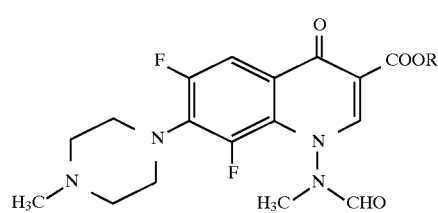 (III)

wherein R is C$_{1-4}$ alkyl.

* * * * *